US010351851B2

(12) United States Patent
Hu et al.

(10) Patent No.: US 10,351,851 B2
(45) Date of Patent: Jul. 16, 2019

(54) METHODS AND COMPOSITIONS FOR ENHANCING THE THERAPEUTIC EFFECT OF ANTI-TUMOR T CELLS

(71) Applicant: The Wistar Institute of Anatomy and Biology, Philadelphia, PA (US)

(72) Inventors: Hui Hu, Wynnewood, PA (US); Jose R. Conejo-Garcia, Philadelphia, PA (US); Tom-Li Stephen, Philadelphia, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 15/855,507

(22) Filed: Dec. 27, 2017

(65) Prior Publication Data

US 2018/0142242 A1 May 24, 2018

Related U.S. Application Data

(60) Continuation of application No. 14/955,539, filed on Dec. 1, 2015, now Pat. No. 9,868,951, which is a division of application No. 14/350,588, filed as application No. PCT/US2012/061556 on Oct. 24, 2012, now Pat. No. 9,226,936.

(60) Provisional application No. 61/552,630, filed on Oct. 28, 2011.

(51) Int. Cl.
| | |
|---|---|
| *A61K 39/00* | (2006.01) |
| *A61K 45/06* | (2006.01) |
| *A61K 35/17* | (2015.01) |
| *C12N 15/113* | (2010.01) |
| *A61K 31/713* | (2006.01) |
| *A61K 38/20* | (2006.01) |
| *A61K 39/395* | (2006.01) |
| *A61N 5/10* | (2006.01) |
| *A61K 47/59* | (2017.01) |
| *A61K 48/00* | (2006.01) |

(52) U.S. Cl.
CPC .......... *C12N 15/113* (2013.01); *A61K 31/713* (2013.01); *A61K 35/17* (2013.01); *A61K 38/2046* (2013.01); *A61K 39/0011* (2013.01); *A61K 39/3955* (2013.01); *A61K 45/06* (2013.01); *A61K 47/595* (2017.08); *A61N 5/10* (2013.01); *A61K 48/005* (2013.01); *A61K 2039/5156* (2013.01); *A61K 2039/5158* (2013.01); *C12N 2310/14* (2013.01); *C12N 2310/531* (2013.01); *C12N 2330/50* (2013.01); *C12N 2740/16043* (2013.01)

(58) Field of Classification Search
CPC .............. A61K 31/713; A61K 31/0611; A61K 2039/5158; C12N 15/14; C12N 15/113
USPC ........ 424/93.21, 277.1; 435/6.1, 91.1, 91.31, 435/325, 375, 455, 458; 514/44; 536/23.1, 24.5
See application file for complete search history.

(56) References Cited

U.S. PATENT DOCUMENTS

| | | | |
|---|---|---|---|
| 6,083,716 A | 7/2000 | Wilson | |
| 6,649,170 B1 | 11/2003 | Lindblad | |
| 7,247,472 B2 | 7/2007 | Wilson | |
| 7,696,179 B2 | 4/2010 | Lieberman | |
| 7,803,611 B2 | 9/2010 | Roelvink | |
| 7,906,111 B2 | 3/2011 | Wilson | |
| 8,026,225 B2 | 9/2011 | Addepalli | |
| 9,226,936 B2 | 1/2016 | Hu | |
| 2007/0154931 A1* | 7/2007 | Radich ................. | C12Q 1/6886 435/6.11 |
| 2010/0317713 A1 | 12/2010 | Olson | |
| 2011/0178159 A1 | 7/2011 | Gu | |
| 2016/0083728 A1 | 3/2016 | Hu | |

FOREIGN PATENT DOCUMENTS

| | | | |
|---|---|---|---|
| WO | WO-2001/040303 | 6/2001 | |
| WO | WO-2004/022103 | 3/2004 | |
| WO | WO-2004/058805 | 7/2004 | |
| WO | WO-2005/095447 | 10/2005 | |
| WO | WO-2005095447 A2 * | 10/2005 | ......... C07K 14/4702 |
| WO | WO-2007/149521 | 12/2007 | |
| WO | WO-2008/154399 | 12/2008 | |
| WO | WO-2010/003002 | 1/2010 | |
| WO | WO-2010/108126 | 9/2010 | |
| WO | WO-2011/130624 | 10/2011 | |
| WO | WO-2012/061556 | 5/2012 | |
| WO | WO-2013/158290 | 10/2013 | |

OTHER PUBLICATIONS

Chen et al (Plos One, vol. 6, No. 5, e20475, pp. 1-7 (May 2011) (Year: 2011).*
Kalos et al (Sci. Tranl. Med., vol. 3, No. 95, (95ra73), pp. 1-8 (Aug. 2011) (Year: 2011).*
Feng et al (Nature Immunol., vol. 12, No. 6, pp. 544-551 (Jun. 2011)) (Year: 2011).*
Arts, Adenoviral vectors for expressing siRNAs for discovery and validation of gene function, Genome Research, 13(10):2325-32, Oct. 2003; e-publication: Sep. 2003.

(Continued)

*Primary Examiner* — Jane J Zara
(74) *Attorney, Agent, or Firm* — Howson & Howson LLP; Mary E. Bak

(57) ABSTRACT

Compositions, e.g., therapeutic agents, and methods are provided for modulating gene and protein expression of Forkhead Box protein 1 (Foxp1). The therapeutic agents include short nucleic acid molecules that modulate gene and protein expression of Forkhead Box protein 1 (Foxp1) expression, viral vectors containing such molecules, T cells transduced with these viruses for adoptive therapies, and any small molecules that bind to and inactivate Foxp1. These compounds and methods have applications in cancer therapy either alone or in combination with other therapies that stimulate the endogenous immune system in the environment of the cancer, e.g., tumor.

8 Claims, 5 Drawing Sheets
Specification includes a Sequence Listing.

(56) References Cited

OTHER PUBLICATIONS

Bollard, Complete responses of relapsed lymphoma following genetic modification of tumor-antigen presenting cells and T-lymphocyte transfer, Blood, 110(8):2838-45, Oct. 15, 2007; e-publication: Jul. 3, 2007.
Bot, Forkhead box protein P1 as a downstream target of transforming growth factor induces collagen synthesis and correlates with a more stable plaque phenotype, Atherosclerosis, 218(1):33-43; May 25, 2011.
Chen, Transcription Factors E2A, FOX01 and FOXP1 Regulate Recombination Activating Gene Expression in Cancer Cells, PLOS One, 6(5):1-7; May 31, 2011.
Chinnasamy, A TCR targeting the HLA-A*0201-restricted epitope of MAGE-A3 recognizes multiple epitopes of the MAGE-A antigen superfamily in several types of cancer, Journal of Immunology, 186(2):685-96, Jan. 15, 2011; e-publication: Dec. 13, 2010.
Conejo-Garcia, Tumor-infiltrating dendritic cell precursors recruited by a beta defensin contribute to vasculogenesis under the influence of Vegf-A, Nature Medicine, 10(9):950-958, Sep. 2004; e-publication: Aug. 29, 2004.
Cubillos-Ruiz, Polyethylenimine-based siRNA nanocomplexes reprogram tumor-associated dendritic cells via TLR5 to elicit therapeutic antitumor immunity, Journal of Clinical Investigations, 119(8):2231-2244; Aug. 2009.
Cubillos-Ruiz, Nanomolecular treating of dendritic cells for ovarian cancer therapy, Future Oncology, 5:1189-1192, Oct. 2009.
Dudley, Cancer regression and autoimmunity in patients after clonal repopulation with antitumor lymphocytes, Science, 298:850-854, Oct. 25, 2002; e-publication: Sep. 19, 2002.
Ebert, MicroRNA sponges: competitive inhibitors of small RNAs in mammalian cells, Nature Methods, 4:721-726, e-publication: Aug. 12, 2007.
Feng, Foxp1 is an essential transcriptional regulator for the generation of quiescent naïve T cells during thymocyte development, Blood, 115(3):510-518; Jan. 21, 2010; e-publication: Nov. 12, 2009.
Feng, Transcription factor Foxp1 exerts essential cell-intrinsic regulation of the quiescence of naïve T cells, Nature Immunology, 12(6):544-551; Jun. 2011, e-publication May 1, 2011.
Feng, Wistar Researchers: Direct Proof of How T Cells Stay in "Standby" Mode, URL: http://www.wistar.org/news-and-media/press-releases/wistar-researchers-direct-proof-how-t-cells-stay-stsandby-mode; May 5, 2011.
Fondell, On the mechanism of non-allelically excluded $V_\alpha$-$J_\alpha$ T cell receptor secondary rearrangements in a murine T cell lymphoma, Journal of Immunology, 144(3):1094-1103, Feb. 1, 1990.
Gao, Novel Adeno-Associated Viruses From Rhesus Monkeys as Vectors for Human Gene Therapy, Proceedings of the National Academy of Sciences, vol. 99, No. 18, pp. 11854-11859, Sep. 3, 2002; e-publication: Aug. 21, 2002.
Grimm, Adeno-associated virus vectors for short hairpin RNA expression, Methods in Enzymology, 392:381-405, 2005.
Huston, 1988, Protein engineering of antibody binding sites: Recovery of specific activity in an anti-digoxin single-chain Fv analogue produced in *Escherichia coli*, Proceedings of the National Academy of Sciences USA 85:5879-5883, Aug. 1988.
Ikonomidis, Delivery of a viral antigen to the class I processing and presentation pathway by Listeria monocytogenes, Journal of Experimental Medicine, 180(6):2209-18, Dec. 1, 1994.
Jiang, Cell biology of IL-7, a key lymphotrophin, Cytokine & Growth Factor Reviews, 16:513-533, Aug.-Oct. 2005.
Kalos, T cells with chimeric antigen receptors have potent antitumor effects and can establish memory in patients with advanced leukemia, Science Translational Medicine, 3(95):95ra73, Aug. 10, 2011.
Kershaw, A phase I study on adoptive immunotherapy using gene-modified T cells for ovarian cancer, Clinical Cancer Research, 12(20 Pt 1):6106-15, Oct. 15, 2006.
Kolb-Mäurer, Listeria monocytogenes-infected human dendritic cells: uptake and host cell response, Infection & Immunity, 68(6):3680-8, Jun. 2000.
Lauer, Constitutive Activation of the PrfA regulon enhances the potency of vaccines based on live-attenuated and killed but metabolically active Listeria monocytogenes strains, Infection Immunity, 76(8):3742-53, Aug. 2008.
Leen, Monoculture-derived T lymphocytes specific for multiple viruses expand and produce clinically relevant effects in immunocompromised individuals, Nature Medicine, 12:1160-1166, Oct. 2006; e-publication: Sep. 24, 2006.
Manjunath, Lentiviral delivery of short hairpin RNAs, Advances in Drug Delivery Reviews, 61(9):732-745, Jul. 25, 2009.
Markey, Conventional dendritic cells are the critical donor APC presenting alloantigen after experimental bone marrow transplantation, Blood, 113:5644-5649, Mar. 31, 2009.
Mazzucchelli, Interleukin-7 receptor expression: intelligent design, Nature Reviews in Immunology, 7:144-154, Feb. 2007.
Milone, Chimeric Receptors Containing CD137 Signal Transduction Domains Mediate Enhanced Survival of T Cells and Increased Antileukemic Efficacy In Vivo, Molecular Therapy, 17(8):1453-1464, Aug. 2009.
Moon, Expression of a functional CCR2 receptor enhances tumor localization and tumor eradication by retargeted human t cells expressing a mesothelin-specific chimeric antibody receptor, Clinical Cancer Research, 17(14):4719-30, Jul. 15, 2011; e-publication: May 24, 2011.
Morgan, Cancer regression in patients after transfer of genetically engineering lymphocytes, Science, 314(5796):126-9, Oct. 6, 2006; e-publication: Aug. 31, 2006.
Nesbeth, Harnessing the effect of adoptively transferred tumor-reactive T cells on endogenous (host-derived) antitumor immunity, Clinical and Developmental Immunology, 2010: 139-304, 2010, e-publication: Nov. 7, 2010.
Nesbeth, CCL5-Mediated Endogenous Antitumor Immunity Elicited by Adoptively Transferred Lymphocytes and Dendritic Cell Depletion, Cancer Research, 69(15):6331-6338; Aug. 1, 2009; e-publication: Jul. 14, 2009.
Nesbeth, CD4+ T cells elicit Host Immune Responses to MHC Class II− Ovarian Cancer through CCL5 Secretion and CD40-Mediated Licensing of Dendritic Cells, The Journal of Immunology, 184(10):5654-5662; May 2010.
Parkhurst, T Cells targeting carcinoembryonic antigen can mediate regression of metastatic colorectal cancer but induce sever transient colitis, Molecular Therapy, 19(3):620-626, Mar. 2011; e-publication: Dec. 14, 2010.
Perez, Establishment of HIV-1 resistance in CD4+ T cells by genome editing using zinc-finger nucleases, Nature Biotechnology, 26(7):808-16, Jul. 2008; e-publication: Jun. 29, 2008.
Porter, Chimeric Antigen Receptor-Modified T Cells in Chronic Lymphoid Leukemia, New England Journal of Medicine, 365(8):725-733; Aug. 10, 2011.
Rao, MicroRNA-34a Perturbs B Lymphocyte Development by Repressing the Forkhead Box Transcription Factor Foxp1, Immunity, 33(1):48-59; Jul. 23, 2010.
Robbins, Tumor regression in patients with metastatic synovial cell sarcoma and melanoma using genetically engineering lymphocytes reactive with NY-ESO-1, Journal Clinical Oncology, 29(7):917-24, Mar. 1, 2011; e-publication: Jan. 31, 2011.
Rutledge, Infectious Clones and Vectors Derived from Adeno-Associated Virus (AAV) Serotypes Other Than AAV Type 2, Journal of Virology, 72(1):309-319, Jan. 1998.
Scarlett, Ovarian cancer progression is controlled by phenotypic changes in dendritic cells, Journal Experimental Medicine, 209(3):495-506, Mar. 12, 2012; e-publication: Feb. 20, 2012.
Scarlett, In situ stimulation of CD40 and toll-like receptor 3 transforms ovarian cancer-infiltrating dendritic cells from immunosuppressive to immunostimulatory cells, Cancer Research, 69:7329-7337, 2009; e-publication: Sep. 8, 2009.
Schrieber, Cancer immunoediting: integrating immunity's roles in cancer suppression and promotion, Science, 331(6024):1565-1570, Mar. 25, 2011.

(56) References Cited

OTHER PUBLICATIONS

Skon, Fox factors fight over T cell quiescence, Nature Immunology, 12(6):522-524; Jun. 2011.

Song, In vivo persistence, tumor localization and antitumor activity of CAR-engineering T cells is enhanced by costimulatory signaling through CD137 (4-1BB), Cancer Research, 71(13):4617-27, Jul. 1, 2011; e-publication: May 5, 2011.

Wang, Multiple domains define the expression and regulatory properties of Foxp1 forkhead transcriptional repressors, 278(27):24259-24268, Jul. 4, 2003, e-publication: Apr. 10, 2003.

Westwood, Adoptive transfer to T cells modified with a humanized chimeric receptor gene inhibits growth of Lewis-Y-expressing tumors in mice, Proceedings National Academy of Sciences, USA, 102(52):19051-19056, Dec. 27, 2005.

Bird, RE et al, Single-chain antigen-binding proteins, Science, 242(4877):423-426, Oct. 21, 1988.

Park, Treating cancer with genetically engineered T cells, Trends Biotechnology, 29(11):550-7, Nov. 2011; e-publication: Jun. 12, 2011.

Sharp, P., MIT's Phillip Sharp discusses microRNA sponges, Gene Silencing News, Aug. 16, 2007.

Wang, H. The transcription factor Foxp1 is a critical negative regulator of the differentiation of follicular helper T cells, Nat. Immunol., Jul 2014, 15(7): 667-675.

Durai, S. et al., Zinc Finger Nucleases: Custom-Designed Molecular Scissors for Genome Engineering of Plant and Mammalian Cells, Nucleic Acids Research, Oct. 2005, 33(18): 5978-5990.

Kandavelou, K. et al., Custom-Designed Molecular Scissors for Site-Specific Manipulation of the Plant and Mammalian Genomes, Methods in Molecular Biology, May 2009, 544: 617-636.

Osborn, M.J. et al., Synthetic zinc finger nuclease design and rapid assembly, Human Gene Therapy, Sep. 2011, 22(9): 1155-1165.

International Search Report dated Mar. 1, 2012 issued in corresponding International Patent Application No. PCT/US2012/061556.

International Preliminary Report on Patentability dated Mar. 1, 2013 issued in corresponding International Patent Application No. PCT/US2012/061556.

International Search Report dated Jun. 24, 2013 issued in related International Patent Application No. PCT/US2013/032027.

\* cited by examiner

Tumor-associated CTLs up-regulate Foxp1 during tumor progression

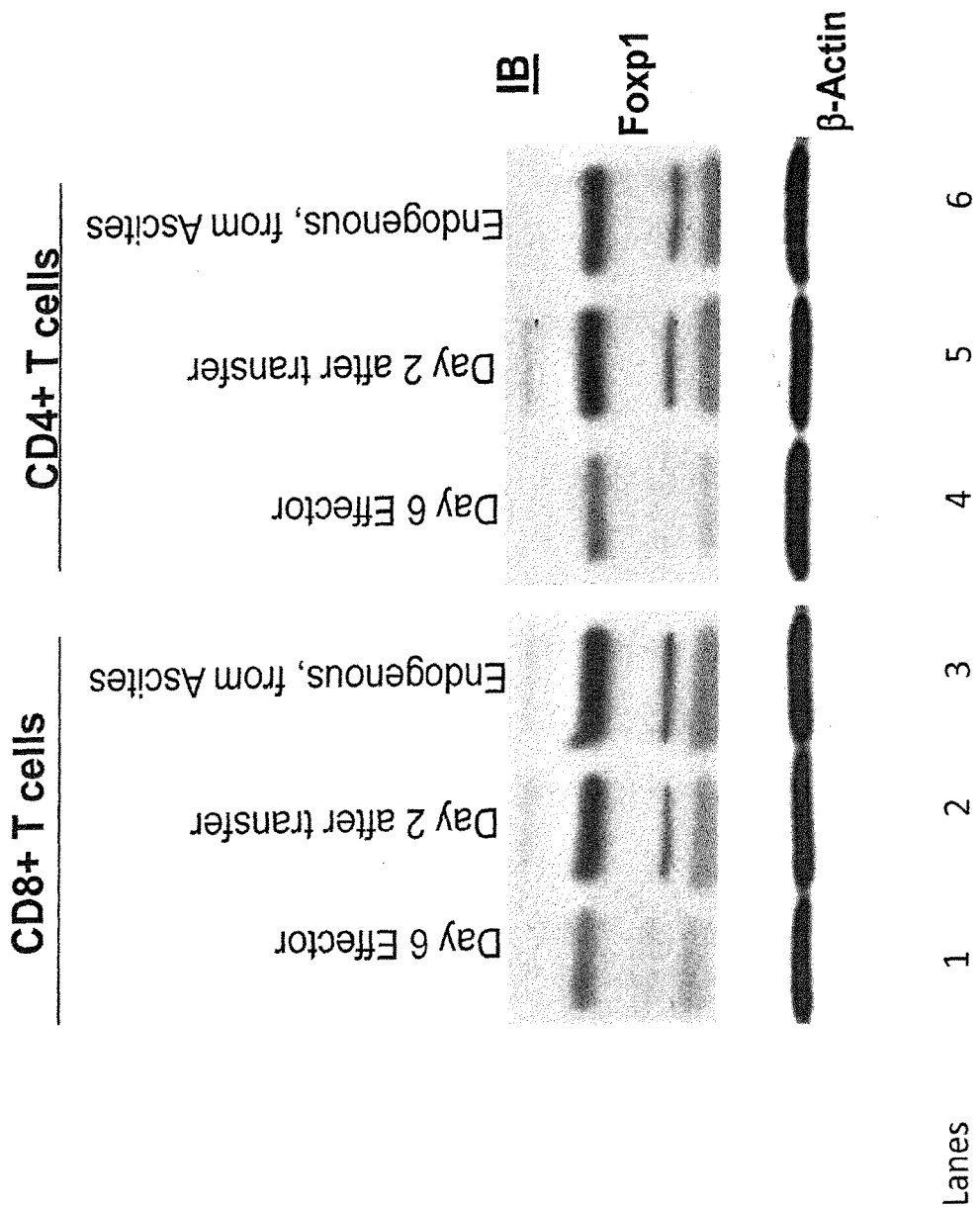

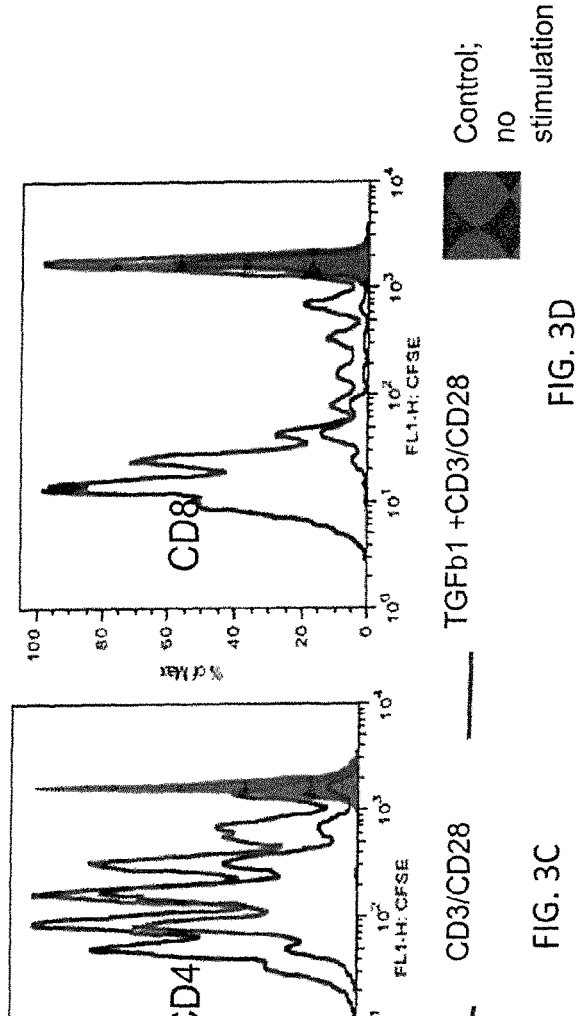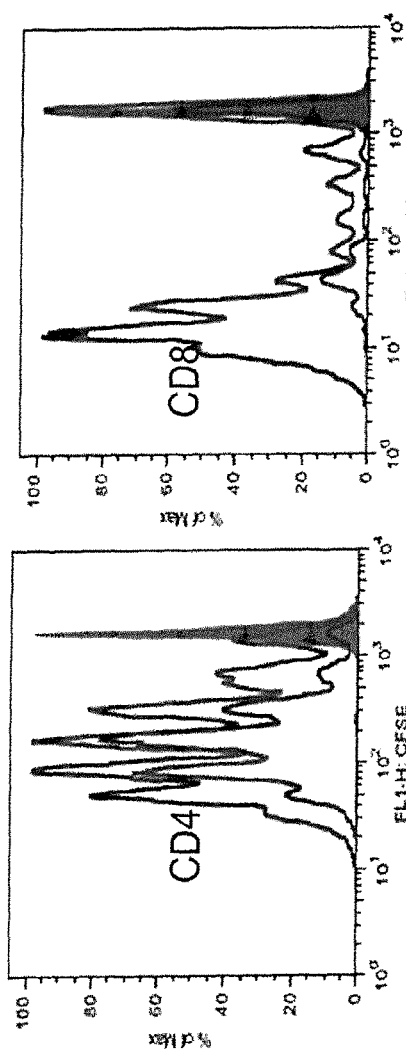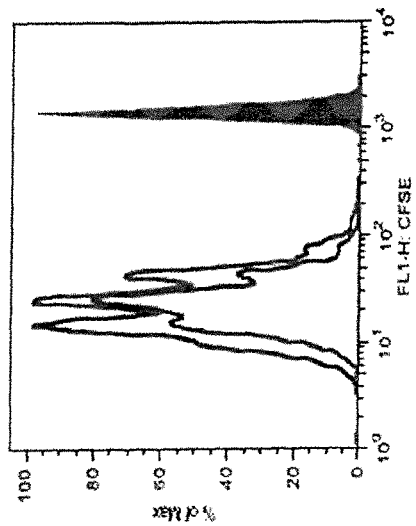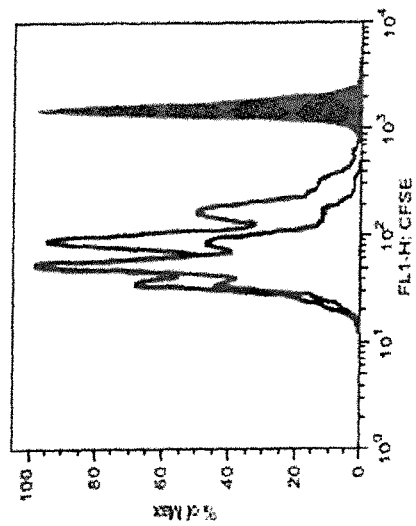

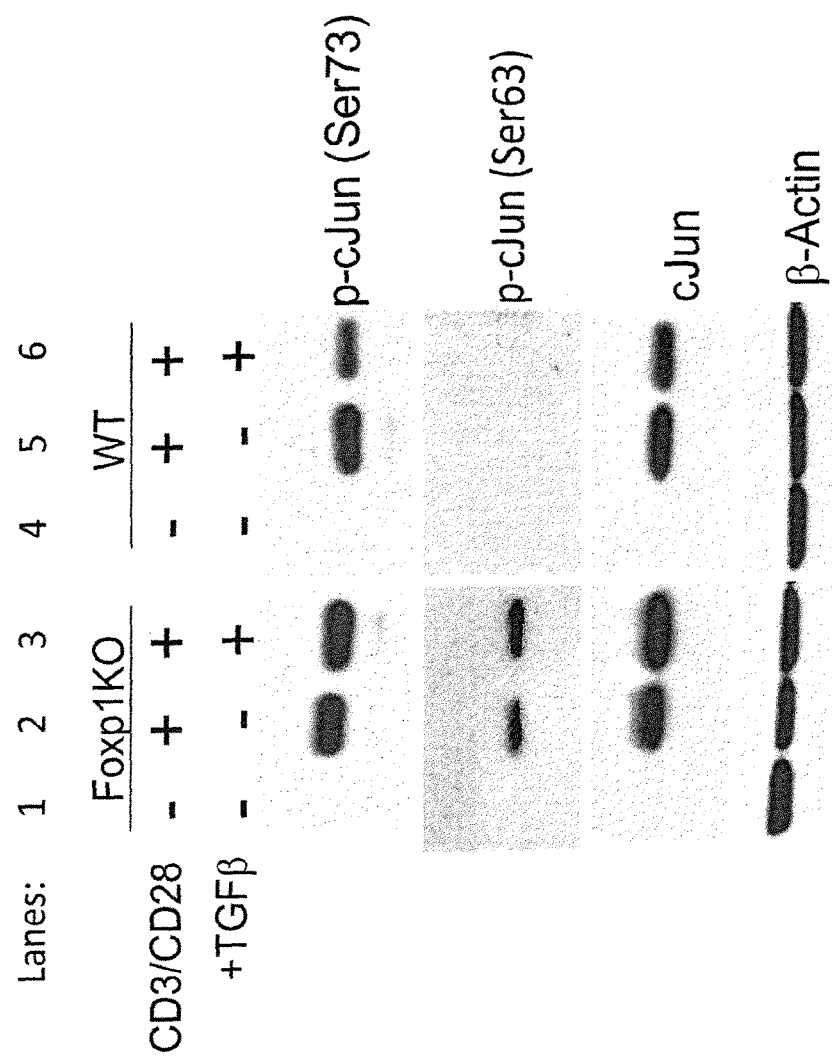

METHODS AND COMPOSITIONS FOR ENHANCING THE THERAPEUTIC EFFECT OF ANTI-TUMOR T CELLS

CROSS-REFERENCE TO RELATED APPLICATIONS

This application is a continuation application of U.S. patent application Ser. No. 14/955,539, filed Dec. 1, 2015, which is a divisional application of U.S. patent application Ser. No. 14/350,588, filed Apr. 9, 2014, now issued as U.S. Pat. No. 9,226,936, which is a 371 national stage of International Patent Application No. PCT/US2012/061556, filed Oct. 24, 2012 (expired), which claims the benefit of the priority of U.S. Provisional Patent Application No. 61/552,630, filed Oct. 28, 2011, which applications are incorporated herein by reference.

STATEMENT REGARDING FEDERALLY SPONSORED RESEARCH OR DEVELOPMENT

This invention was made with government support under Grant Nos. R01CA124515 and 1K22AI070317-01A1 awarded by the National Institutes of Health. The government has certain rights in this invention.

INCORPORATION-BY-REFERENCE OF MATERIAL SUBMITTED IN ELECTRONIC FORM

Applicant hereby incorporates by reference the Sequence Listing material filed in electronic form herewith. This file is labeled "WST128C1US_ST25.txt".

BACKGROUND OF THE INVENTION

Tumors are imprinted by their immune environment, and this imprinting facilitates their transformation into populations that can more effectively resist the pressure exerted by the subject's immune system to eradicate them. The immune system can act both positively to inhibit the progression of tumors and negatively to mold the establishment of tumors that can evade its recognition, or worse to promote the advancement of tumor development. This process by which the immune system can prevent or promote tumor progression is referred to as immunoediting (Schreiber R D et al, 2011, Science, 331(6024):1565-70; Scarlett U K et al, 2012, J. Exp. Med., 209(3):495-506).

Adoptive cell transfer therapy (ACT) or Adoptive T cell therapy is the ex vivo activation, expansion, and subsequent administration of tumor-reactive T cells. Adoptive T cell therapies have focused on the use of CD8+ T cells, as they have relatively long clonal expansion times, can specifically target tumors, and are easily subjected to genetic manipulations. Adoptively transferred tumor-specific T cells can also be expanded from resected tumors before being genetically manipulated. Under ideal circumstances, transferred T cells migrate to the tumor site and directly lyse tumor cells, while releasing endogenous immune cells from tumor-induced immunosuppression. However, the tumor environment is usually so immunosuppressive that it is difficult to appropriately release these brake mechanisms on antitumor responses.

Adoptive T cell therapy, while highly successful for many nonepithelial cancers, has not yet been effective in the most frequent and aggressive epithelial cancers, including ovarian carcinoma (see, e.g., Kershaw, M. H. et al. 2006 Clin Cancer Res 12, 6106-15; see also, Dudley M E et al 2002 Science 298, 850-4; Bollard, C M et al 2007 Blood, 100:2838-45; Leen, A M et al 2006 Nat. Med., 12:1160-6). Tumor-reactive T cells properly conditioned ex vivo have the capacity to induce significant therapeutic effects against preclinical models of established ovarian cancer (Nesbeth Y, S. Y., et al, 2009 Cancer Res. 69, 6331-38; Nesbeth, Y. C. et al. 2010 J Immunol 184, 5654-62). Nevertheless, in these studies, anti-tumor T cells did not persist for long periods and, despite a significant survival increase, mice eventually succumbed to the disease, suggesting that the activity of transplanted T cells was suboptimal. This lack of success is likely due to the complexities of the tumor microenvironment, which apparently causes the rapid disappearance of transferred lymphocytes. Supporting this proposition, the responsiveness of tumor-reactive T cells in lymph nodes draining established tumors is severely impaired during tumor progression (PMID: 22351930).

Further, the ability to produce large numbers of tumor-reactive T cells is hampered because not only do they usually occur in only low frequencies, but also most T cells that robustly respond to self-antigens have either been eliminated during thymic development or rendered nonfunctional by local tolerizing mechanisms.

There remains a need in the art for effective adoptive immunotherapy mechanisms for the successful treatment of a variety of cancers.

SUMMARY OF THE INVENTION

In one aspect, a method for enhancing the anti-tumor response in a subject having a cancer, such as a cancer characterized by a solid tumor, involves administering to a subject in need thereof a therapeutic reagent that down-regulates the expression of Foxp1 in T cells.

In another aspect, the method employs a therapeutic reagent that includes a short nucleic acid molecule comprising a nucleotide sequence that is complementary to at least a portion of the nucleotide sequence encoding FoxP1. In certain embodiments, this short nucleic acid molecule is a short hairpin RNA (shRNA) or a short interfering RNA (siRNA).

In another aspect, the method employs as the therapeutic agent a plasmid or viral vector that comprises the short nucleic acid molecule, e.g., an shRNA, that comprises a sequence that is complementary to at least a portion of the nucleotide sequence encoding FoxP1, under the control of regulatory sequences. In another embodiment, the viral vector is complexed with a polymer to create a nanoparticle.

In another aspect, the method employs a therapeutic agent that is a T cell that is transduced or transfected ex vivo with the above-described viral vector/plasmid. In this method, the T cell is adoptively transferred into the subject. In still another embodiment, the transduced T cell is pulsed with tumor antigen prior to transduction with the viral vector/plasmid comprising the shRNA sequence that is complementary to at least a portion of the nucleotide sequence encoding FoxP1. In still another embodiment, the T cell is transduced or transfected with a construct that expresses another anti-cancer therapeutic agent, e.g., IL-7.

In another aspect, the method employs a therapeutic agent that is a T cell pulsed with cancer/tumor-specific antigen, transduced with a vector expressing a TCR or chimeric receptor and treated with a zinc-finger nuclease that targets a unique sequence of Foxp1 and removes it from the cells. In this method, the T cell is adoptively transferred into the subject.

In another aspect, the method employs as the therapeutic agent a synthetic siRNA oligonucleotide comprising a sequence that is complementary to at least a portion of the nucleotide sequence encoding FoxP1. In one embodiment, the siRNA is in the form of a nanoparticle.

In still another aspect, the methods described above further involve administering or co-administering another anti-cancer therapeutic agent, e.g., a chemotherapeutic molecule or a cytokine, e.g., IL-7.

In still another aspect, the methods described above further involve administering the therapeutic agent before, during or after, surgery to remove or debulk a tumor. In still another aspect, the methods described above further involve administering the therapeutic agent before, during or after, a course of therapeutic radiation. In still another aspect, the methods described above further involve administering the therapeutic agent before, during or after, a course of chemotherapy.

In still another aspect, a method of preparing a therapeutic composition comprises pulsing T cells with a selected cancer antigen or tumor-specific antigen; and transducing said pulsed T cells with a vector expressing a construct that down regulates Foxp1, and formulating said pulsed, transfected T cells with a suitable pharmaceutical carrier.

In still another aspect, a therapeutic or prophylactic composition comprises a viral vector that targets specifically T cells, the vector expressing a construct that inhibits the expression of Foxp1, and a pharmaceutically acceptable carrier or diluent. In one embodiment, the construct is a short hairpin (shRNA) sequence that suppresses the expression of Foxp1.

In still another aspect, a therapeutic or prophylactic composition comprises a T cell transduced or transfected ex vivo with a viral vector, as described above, wherein the expression of Foxp1 in the T cell is extinguished or reduced.

Other aspects and advantages of these compositions and methods are described further in the following detailed description of the preferred embodiments thereof.

BRIEF DESCRIPTION OF THE DRAWINGS

FIG. 2 are Western blots quantifying Foxp1 in samples of CD8+T and CD4+ T cells and showing that Foxp1 is up-regulated in effector T cells in the tumor microenvironment: lanes 1 and 4: naïve, negatively immunopurified T cell splenocytes, primed against tumor antigen for 7 days by incubation with bone marrow-derived dendritic cells pulsed with double (UV+gamma) irradiated tumor cells (Day 6 effectors); lanes 2 and 5: adoptively transferred (CD45.2+) CD8 cells and CD4 T cells, respectively, FACS-sorted from peritoneal wash samples of CD45.1 (congenic) advanced ID8-Defb29/Vegf-a tumor-bearing mice that had received tumor antigen-primed T cells 2 days before sacrifice (Day 2 after transfer); and lanes 3 and 6: endogenous (host-derived, CD45.1) tumor-associated T cells FACS-sorted from peritoneal wash samples of CD45.1 (congenic) advanced ID8-Defb29/Vegf-a tumor-bearing mice that had received tumor antigen-primed T cells 2 days before sacrifice (endogenous, from ascites).

FIG. 3A is a chromatograph trace obtained when naïve, negatively immunopurified CD4 T cell splenocytes from wild-type Cre⁻ mice were CFSE-labeled and expanded in the presence of CD3/CD28 Ab-coated beads (dark line; Invitrogen). When indicated, 5 ng/mL of TGFβ was added (light gray line), and CFSE dilution (indicative of T cell proliferation) was monitored by flow cytometry. Gray shading shows the present of a control with no stimulation. Foxp1 T cells are resistant to the abrogation of T cell expansion induced by TGFβ.

FIG. 3B is a chromatograph trace obtained when naïve, negatively immunopurified CD8 splenocytes from wild-type Cre⁻ mice were CFSE-labeled and expanded in the presence of CD3/CD28 Ab-coated beads (dark line; Invitrogen). When indicated, 5 ng/mL of TGFβ was added (light gray line), and CFSE dilution (indicative of T cell proliferation) was monitored by flow cytometry. Gray shading shows the present of a control with no stimulation. Foxp1 T cells are resistant to the abrogation of T cell expansion induced by TGFβ.

FIG. 3C shows the results of the protocol of FIG. 3A in Fox p1 KO mice. Mice with no Foxp1 T cells display abrogation of T cell expansion induced by TGFβ.

FIG. 3D shows the results of the protocol of FIG. 3B in Foxp1 KO mice. Mice with no Foxp1 T cells display abrogation of T cell expansion induced by TGFβ.

FIG. 4 shows Western blot analysis of total and phosphorylated c-Jun in Lane 1: naïve, negatively immunopurified, unstimulated CD8 T cell splenocytes of Foxp1 KO mice; Lane 2: naïve, negatively immunopurified, CD8 T cell splenocytes of Foxp1 KO stimulated for 24 hours in the presence of CD3/CD28 Ab-coated beads; Lane 3: naïve, negatively immunopurified, CD8 T cell splenocytes of Foxp1 KO stimulated in the presence of CD3/CD28 Ab-coated beads with 5 ng/mL of TGFβ added to the wells; Lane 4: naïve, negatively immunopurified, unstimulated CD8 T cell splenocytes of wildtype mice; Lane 5: naïve, negatively immunopurified, CD8 T cell splenocytes of wild-type mice stimulated in the presence of CD3/CD28 Ab-coated beads; Lane 6: naïve, negatively immunopurified, CD8 T cell splenocytes of wildtype mice stimulated in the presence of CD3/CD28 Ab-coated beads with 5 ng/mL of TGFβ added to the wells. TGFβ represses cJun activation in WT but not in Foxp1 KO CD8+ T cells, as indicated in FIG. 4. Note the induction of c-Jun phosphorylation upon CD3/CD28 activation and how it is selectively abrogated in wild-type T cells in the presence of TGFβ.

DETAILED DESCRIPTION OF THE INVENTION

Figure 1A:
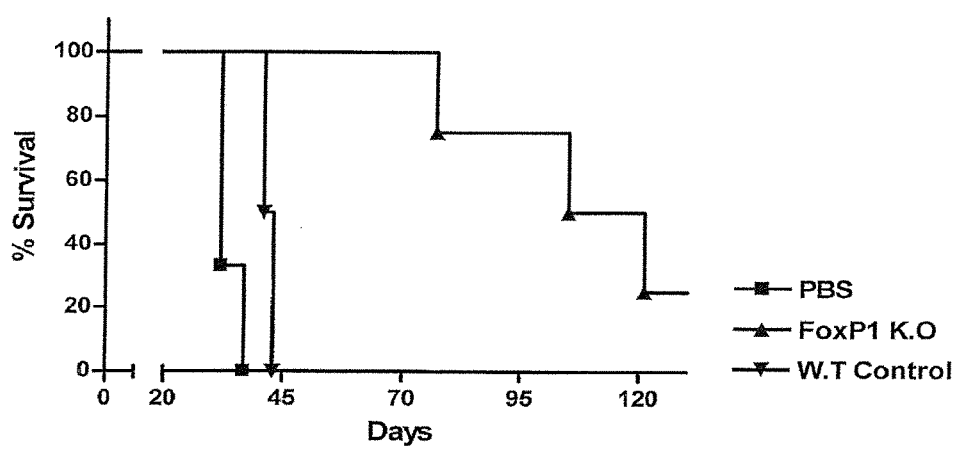
FIG. 1A is a graph showing the results of an experiment described in Example 3 in which anti-tumor Foxp1-deficient T cells (▲) or wild-type T cells(▼) were adoptively administered to a mouse model of ovarian cancer (ID8-Defb29/Vegf-a). Control mice were treated with PBS (■). The adoptive transfer of the anti-tumor Foxp1-deficient T cells to the mouse model stopped ovarian cancer progression for a prolonged period, so that all treated mice showed no signs of disease 6 days after the last mouse treated. Survival was 100% at about 73 days, and at 25% at 120 days. In contrast, administration to the mouse model of PBS or wild-type tumor-reactive T cells resulted in 100% death within 35 or 42 days of administration, respectively.

This invention provides compositions, e.g., therapeutic agents, and methods that modulate gene and protein expression of Forkhead Box protein 1 (Foxp1) expression. The therapeutic agents include short nucleic acid molecules that modulate gene and protein expression of Forkhead Box protein 1 (Foxp1) expression, viral vectors containing such molecules, T cells transduced with these viruses for adoptive therapies, and any small molecules that bind to and inactivate Foxp1. The compounds and methods of the present invention have applications in cancer therapy either alone or in combination with other therapies.

Modulation of the expression of the transcription factor Foxp1 in T cells promote the engraftment and superior therapeutic activity in the hostile microenvironment of the most aggressive and frequent cancers. The compositions and methods described herein are based on the inventors' finding that down-regulating the expression of FoxP1 in anti-tumor T cells enhances their therapeutic effects in the environment of a tumor.

The inventors identified that Foxp1 is upregulated in tumor microenvironmental T cells. In addition, Foxp1-deficient anti-tumor T cells are insensitive to the tolerogenic effect of TGF☐, an immunosuppressive mediator universally present in the microenvironment of virtually all solid tumors. Correspondingly, adoptively transferred Foxp1-deficient tumor-reactive T cells exert significantly superior anti-tumor activity in preclinical models of mice growing established orthotropic ovarian tumors.

Definitions

Technical and scientific terms used herein have the same meaning as commonly understood by one of ordinary skill in the art to which this invention belongs and by reference to published texts, which provide one skilled in the art with a general guide to many of the terms used in the present application. The following definitions are provided for clarity only and are not intended to limit the claimed invention.

The term "target nucleic acid" as used herein means any nucleic acid sequence of FoxP1, whose expression or activity is to be modulated. The target nucleic acid can be DNA or RNA.

The term "hairpin" and "stem-loop" can be used interchangeably and refer to stem-loop structures. The stem results from two sequences of nucleic acid or modified nucleic acid annealing together to generate a duplex. The loop lies between the two strands comprising the stem. The term "loop" refers to the part of the stem-loop between the two homologous regions (the stem) that can loop around to allow base-pairing of the two homologous regions. The loop can be composed of nucleic acid (e.g., DNA or RNA) or non-nucleic acid material(s), referred to herein as nucleotide or non-nucleotide loops. A non-nucleotide loop can also be situated at the end of a nucleotide molecule with or without a stem structure.

The term "complementary" and "complementarity" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). Complete or 100% complementarity refers to the situation in which each nucleotide unit of one polynucleotide strand or region can hydrogen bond with each nucleotide unit of a second polynucleotide strand or region. Complementarities less than 100%, e.g., 95%, 90%, 85%, refers to the situation in which 5%, 10% or 15% of the nucleotide bases of two strands or two regions of a stated number of nucleotides, can hydrogen bond with each other.

The term "gene" as used herein means a nucleic acid that encodes a RNA sequence including but not limited to structural genes encoding a polypeptide.

The term "sense region" as used herein means a nucleotide sequence of a small nucleic acid molecule having complementary to a target nucleic acid sequence. In addition, the sense region of a small nucleic acid molecule can comprise a nucleic acid sequence having homology with a target nucleic acid sequence.

The term "antisense region" as used herein means a nucleotide sequence of a small nucleic acid molecule having a complementarity to a target nucleic acid sequence. It can also comprise a nucleic acid sequence having complementarity to a sense region of the small nucleic acid molecule.

The term "modulate" or "modulates" means that the expression of the gene or level of RNA molecule or equivalent RNA molecules encoding one or more protein or protein subunits or peptides, or the expression or activity of one or more protein subunits or peptides is up regulated or down regulated such that the expression, level, or activity is greater than or less than that observed in the absence of the modulator. The term "modulate" includes "inhibit".

The term "cancer" or "proliferative disease" as used herein means any disease, condition, trait, genotype or phenotype characterized by unregulated cell growth or replication as is known in the art. It can include all types of tumors, lymphomas, carcinomas that can respond to the modulation of disease-related Fox-1 gene expression in a cell or tissue alone or in combination with other therapies. In various embodiments of the methods and compositions described herein, the cancer can include, without limitation, breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, leukemia, myeloma, lymphoma, glioma, and multidrug resistant cancer.

The term "lymphodepletion" is the elimination of suppressive T cell populations, and has been used to enhance the persistence of transferred T cells in vivo. These methods remove cytokine sinks (i.e., endogenous cells that compete with the transferred cells for cytokines that promote their activation and function), and through augmenting the function and availability of APCs, lymphodepletion is thought to enhance the antitumor response.

"Active immunotherapy" is defined as a method in which vaccines such as peptides, tumor antigens, nucleic acids, engineered tumor cells, or tumor-pulsed DCs are used to activate host antitumor immune cells to react against a tumor. Active immunotherapy in both mouse and human tumor systems have resulted in potent antitumor responses and regression, and is beneficial in the fact that rather than restricting responses to a single epitope/antigen, polyclonal responses can readily be induced.

"Passive immunotherapy" methods transfer antibodies or antitumor lymphocytes into tumor-bearing hosts to directly induce tumor cell destruction. Passive immunotherapy has revealed high success rates in certain situations; however, as most protocols direct responses against a single antigen/epitope, and tumors often modulate their expression of particular antigens, there is often a high degree of inefficacy.

As used herein, the term "subject", "patient", or "mammalian subject" includes primarily humans, but can also be extended to include domestic animals, such as dogs and cats, and certain valuable animals, such as horses, farm animals, laboratory animals (e.g., mice, rats) and the like.

As used herein, the term "antibody," refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), diabodies, Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

It should be understood that while various embodiments in the specification are presented using "comprising" language, under various circumstances, a related embodiment is also be described using "consisting of" or "consisting essentially of" language. It is to be noted that the term "a" or "an", refers to one or more, for example, "an anti-tumor T cell" is understood to represent one or more anti-tumor T cells. As such, the terms "a" (or "an"), "one or more," and "at least one" is used interchangeably herein.

II. COMPOSITIONS USEFUL IN THE INVENTION

As disclosed herein, the compositions described herein modulate the expression of, or target, Foxp1. The forkhead box (Fox) proteins constitute a large transcription factor family with diverse functions in development, cancer and aging. Foxp1, a member of the 'Foxp' subfamily, is expressed in many tissues and is a critical transcriptional regulator in B lymphopoiesis. Conditional deletion of Foxp1 at the CD4+CD8+ double-positive (DP) thymocyte stage has proven that Foxp1 is essential for the generation of quiescent naive T cells during thymocyte development (Feng et al, 2010 Blood, 115:510-518). In addition, Foxp1 expression increases in tumor-associated T cells during cancer progression.

NCBI Gene ID No. 27086 provides the human gene information for the Foxp1 gene of *homo sapiens*. One transcript variant of the 7102 bp human FOXP1 mRNA sequence is reported at NBCI Reference Sequence NM_032682.5 (SEQ ID NO: 1). The protein coding region spans nt 527 through nt 2560 of SEQ ID NO: 1, encoding a 677 amino acid protein SEQ ID NO: 2. Other variants are known and can be obtained commercially from e.g., GeneCopoeia, among other commercial sources. Similarly one may obtain murine nucleotide and protein sequences of FoxP1 from similar sources (see e.g., NCBI Ref Nos. NM_001197322.1, NM_053202.1 and BC064764.1). All such published sequences for FoxP1 variants are incorporated herein by reference.

In one embodiment, the compositions and methods described herein target Foxp1 as set forth in SEQ ID NO: 1. Thus in some embodiments, the term "Foxp1" refers to any Foxp1 protein, peptide, or polypeptide or isoform, including naturally occurring or deliberated mutated or genetically engineered sequences, having Foxp1 family activity such as encoded by SEQ ID NO: 1. In other embodiments, the term Foxp1 includes any nucleic acid sequence encoding a Foxp1 protein, peptide, or polypeptide of mammalian origin, including naturally occurring or deliberated mutated or genetically engineered sequences. In still other embodiments, Foxp1-related molecules include polymorphisms or single nucleotide polymorphisms of Foxp1, Foxp1 homologs, and Foxp1 splice and transcript variants. Other human isoforms of Foxp1, isoforms 1-8 are identified under the NCBI Gene ID No. 27086.

The compositions described herein can be used to downregulate Foxp1 expression in a subject having a cancer, or more specifically a tumor. A composition or molecule that specifically inhibits Foxp1 can block the immunosuppression of a patient's anti-cancer T cells, and therefore is very useful in therapy directed at the treatment of tumors.

The compositions useful herein can employ a variety of components and be achieved in multiple ways. Table 1 below sets out the SEQ ID Nos for the sequences discussed hereinbelow. Note that the shRNA sequences in the attached sequence listing are expressed as the DNA sequences used to express the shRNA in a vector.

TABLE 1

| SEQ ID NO: | Sequence Type |
|---|---|
| 3 | siRNA for Foxp1 |
| 4 | siRNA for Foxp1 |
| 5 | shRNA1 for Foxp1 |
| 6 | Mature sense strand of shRNA1 |
| 7 | Mature antisense strand of shRNA1 |
| 8 | shRNA2 for Foxp1 |
| 9 | Mature sense strand, shRNA2 |
| 10 | Mature antisense strand, shRNA2 |
| 11 | shRNA3 for Foxp1 |
| 12 | Mature sense strand, shRNA3 |
| 13 | Mature antisense strand, shRNA3 |
| 14 | shRNA4 for Foxp1 |
| 15 | Mature sense strand, shRNA4 |
| 16 | Mature antisense strand, shRNA4 |
| 17 | shRNA5 for Foxp1 |
| 18 | Mature sense strand, shRNA5 |
| 19 | Mature antisense strand, shRNA5 |
| 20 | shRNA6 for Foxp1 |
| 21 | Mature sense strand, shRNA6 |
| 22 | Mature antisense strand, shRNA6 |
| 23 | shRNA7 for Foxp1 |
| 24 | Mature sense strand, shRNA7 |
| 25 | Mature antisense strand, shRNA7 |
| 26 | shRNA8 for Foxp1 |
| 27 | Mature sense strand, shRNA8 |
| 28 | Mature antisense strand, shRNA8 |
| 29 | shRNA9 for Foxp1 |
| 30 | Mature sense strand, shRNA9 |
| 31 | Mature antisense strand, shRNA9 |
| 32 | shRNA10 for Foxp1 |
| 33 | Mature sense strand, shRNA10 |
| 34 | Mature antisense strand, shRNA10 |
| 35 | shRNA11 for Foxp1 |
| 36 | Mature sense strand, shRNA11 |
| 37 | Mature antisense strand, shRNA11 |
| 38 | shRNA12 for Foxp1 |
| 39 | Mature sense strand, shRNA12 |
| 40 | Mature antisense strand, shRNA12 |
| 41 | shRNA13 for Foxp1 |
| 42 | Mature sense strand, shRNA13 |
| 43 | Mature antisense strand, shRNA13 |
| 44 | shRNA14 for Foxp1 |

TABLE 1-continued

| SEQ ID NO: | Sequence Type |
|---|---|
| 45 | Mature sense strand, shRNA14 |
| 46 | Mature antisense strand, shRNA14 |
| 47 | shRNA15 for Foxp1 |
| 48 | Mature sense strand, shRNA15 |
| 49 | Mature antisense strand, shRNA15 |
| 50 | shRNA16 for Foxp1 |
| 51 | Mature sense strand, shRNA16 |
| 52 | Mature antisense strand, shRNA16 |
| 53 | shRNA17 for Foxp1 |
| 54 | Mature sense strand, shRNA17 |
| 55 | Mature antisense strand, shRNA17 |

Short Nucleic Acid Molecules

A short nucleic acid molecule useful in the compositions and in the methods described herein is any nucleic acid molecule capable of inhibiting or down-regulating FoxP1 gene expression. Typically, short interfering nucleic acid molecules are composed primarily of RNA, and include siRNA or shRNA, as defined below. A short nucleic acid molecule may, however, include nucleotides other than RNA, such as in DNAi (interfering DNA), or other modified bases. Thus, the term "RNA" as used herein means a molecule comprising at least one ribonucleotide residue and includes double stranded RNA, single stranded RNA, isolated RNA, partially purified, pure or synthetic RNA, recombinantly produced RNA, as well as altered RNA such as analogs or analogs of naturally occurring RNA. In one embodiment the short nucleic acid molecules of the present invention is also a short interfering nucleic acid (siNA), a short interfering RNA (siRNA), a double stranded RNA (dsRNA), a micro RNA (.mu.RNA), and/or a short hairpin RNA (shRNA) molecule. The short nucleic acid molecules can be unmodified or modified chemically. Nucleotides of the present invention can be chemically synthesized, expressed from a vector, or enzymatically synthesized.

In some embodiments, the short nucleic acid comprises between 18 to 60 nucleotides. In another embodiment, the short nucleic acid molecule is a sequence of nucleotides between 25 and 50 nucleotides in length. In still other embodiments, the short nucleic acid molecule ranges up to 35 nucleotides, up to 45, up to 55 nucleotides in length, depending upon its structure. These sequences are designed for better stability and efficacy in knockdown (i.e., reduction) of Foxp1 gene expression. In one embodiment, the nucleic acid molecules described herein comprises 19-30 nucleotides complementary to a Foxp1 nucleic acid sense sequence, particularly an open reading frame of Foxp1. In one embodiment, the nucleic acid molecules described herein comprises 19-30 nucleotides complementary to a Foxp1 antisense nucleic acid sequence strand. In one embodiment, the nucleic acid molecules described herein comprises 19-30 nucleotides complementary to a Foxp1 nucleic acid sense sequence and comprises 19-30 nucleotides complementary to a Foxp1 antisense nucleic acid sequence strand.

1. siRNA Molecules

In one embodiment, a useful therapeutic agent is a small interfering RNA (siRNA) or a siRNA nanoparticle. siRNAs are double stranded, typically 21-23 nucleotide small synthetic RNA that mediate sequence-specific gene silencing, i.e., RNA interference (RNAi) without evoking a damaging interferon response. siRNA molecules typically have a duplex region that is between 18 and 30 base pairs in length. FoxP1 siRNAs are designed to be homologous to the coding regions of FoxP1 mRNA (e.g., SEQ ID NO: 1) and suppress gene expression by mRNA degradation. The siRNA associates with a multi protein complex called the RNA-induced silencing complex (RISC), during which the "passenger" sense strand is enzymatically cleaved. The antisense "guide" strand contained in the activated RISC then guides the RISC to the corresponding mRNA because of sequence homology and the same nuclease cuts the target mRNA, resulting in specific gene silencing. The design of si/shRNA preferably avoids seed matches in the 3'UTR of cellular genes to ensure proper strand selection by RISC by engineering the termini with distinct thermodynamic stability. A single siRNA molecule gets reused for the cleavage of many target mRNA molecules. RNAi can be induced by the introduction of synthetic siRNA.

In one embodiment, a siRNA molecule of the invention comprises a double stranded RNA wherein one strand of the RNA is complimentary to the RNA of Foxp1. In another embodiment, a siRNA molecule of the invention comprises a double stranded RNA wherein one strand of the RNA comprises a portion of a sequence of RNA having Foxp1 sequence. SEQ ID Nos: 3 and 4 illustrate two exemplary siRNAs for Foxp1. Synthetic siRNA effects are short lived (a few days) probably because of siRNA dilution with cell division and also degradation.

In one embodiment, siRNA without any chemical modification having high stability and specificity for Foxp1, are useful as therapeutics alone, or in combination with other therapies for cancer. In another embodiment, siRNA oligonucleotides targeting Foxp1 are complexed or conjugated to a polymer or any other material that stabilizes siRNA, for use as therapeutics alone, or in combination with other therapies for cancer.

Among such stabilizing polymers and materials are polyethyleneimine (PEI), which may be conjugated to siRNA, resulting in the generation of nanocomplexes of about 50 nm, as described in Cubillos-Ruiz J R, et al, 2009 J. Clin. Invest., 119(8):2231-44, incorporated by reference herein. In another embodiment, such a stabilizing material is chitosan. In one embodiment, the siRNA is in a stable composition, with or without conjugation, with cholesterol. In still other embodiments, siRNA may be combined with conjugates such as a lipid, a cationic lipid, a phospholipid, and a liposome.

In another embodiment, the siRNA is in a stable composition, with or without conjugation, to an antibody or fragment thereof that permits the siRNA to be preferentially targeted. In one embodiment, the antibody is an antibody or fragment to a desirable molecule, such as an IL7 receptor. In another embodiment, the antibody is an antibody or fragment to a T cell surface marker, a T cell receptor or a chimeric receptor which also permits targeting. For example, in one another embodiment, the siRNA are linked to thiolated F(ab)2 fragments of monoclonal antibodies targeting T cell surface markers (e.g., CD3, CTLA4, CD44, CD69 or CD25).

In another embodiment, the antibody or fragment is to a T cell receptor or chimeric receptor. T cell receptors or chimeric receptors for association with, or co-expression with the siRNA include without limitation, TCRs against human antigens. Among such useful TCRs include those that have been transduced in adoptively transferred T cells (reviewed in Trends Biotechnol. 2011 November; 29(11): 550-7). In one embodiment, the TCR is the receptor that binds human carcinoembryonic antigen (Parkhurst M R et al, 2011 Mol. Ther., 19(3):620-6), NY-ESO-1 (Robbins P F et al, 2011 J. Clin. Oncol., 29(7):917-24), MAGE-A3 (Chinnasamy N et al 2011 J. Immunol., 186(2):685-96) and MART-1, gp100 and p53 (Morgan R A et al, 2006 Science, 314(5796):126-9). Association with such TCRs is described in Westwood et al, 2005, cited herein.

Examples of chimeric receptors useful in the compositions and methods described herein are chimeric receptors against the antigens CD19 (Kolos M, et al, 2011 Sci Transl. Med., 3(95):95ra73) and Epstein Barr virus (Fondell, J D et al, 1990 J. Immunol., 144(3):1094-103). Other chimeric receptors have also targeted mesothelin (Moon E K et al, 2011 Clin Cancer Res., 17(14):4719-30) and the folate receptor (Song D G et al, 2011 Cancer Res., 71(13):4617-27).

2. shRNA Molecules

In another embodiment, the short nucleic acid molecule is a small hairpin RNA (shRNA). An shRNA molecule useful in the methods and compositions described herein is generally defined as an oligonucleotide containing the about 18-23 nucleotide siRNA sequence followed by a ~9-15 nt loop and a reverse complement of the siRNA sequence. The loop nucleotides generally form a non-coding sequence. Examples of commercially available shRNA sequences targeting human Foxp1 include the following DNA sequences along with their mature and antisense strands listed in Table 1. These DNA sequences, when expressed in a vector, form the corresponding shRNA sequences. For example, as demonstrated in shRNA1 for Foxp1 SEQ ID NO: 5, nucleotide positions 21-39 are the mature sense strand, followed by the sequence of nucleotides 42-57 containing the loop and then followed by nucleotides 61-79, which are the antisense strand. The same analysis can be made of the other shRNA sequences in Table 1. Thus, other embodiments of shRNAs include those of SEQ ID NOs: 5, 8, 11, 14, 17, 20, 23, 26, 29, 32, 35, 38, 41, 44, 47, 50 and 53, or their mature or antisense strands.

shRNAs can be cloned in plasmids or in non-replicating recombinant viral vectors to endogenously/intracellularly express shRNA, which is subsequently processed in the cytoplasm to siRNA. The shRNA effects are longer lasting because they are continually produced within the cells and thus have an effect that lasts the duration of the cell's life.

B. Recombinant Vectors Carrying an shRNA Construct

As used herein, a vector may include any genetic element including, without limitation, naked DNA, a phage, transposon, cosmid, episome, plasmid, bacteria, or a virus. As used herein, the term vector refers to a genetic element which expresses, or causes to be expressed, the desired construct that inhibits the expression of Foxp1 in the target cell ex vivo or in vivo.

These shRNAs can be produced in plasmid based systems, of which many are commercially available. However, because they are easy to deliver, non-replicating recombinant viral vectors are commonly used for shRNA expression. Thus, in one embodiment, the vector is a non-pathogenic virus. In another embodiment, the vector is a non-replicating virus. In one embodiment, a desirable viral vector may be a retroviral vector, such as a lentiviral vector. In another embodiment, a desirable vector is an adenoviral vector. In still another embodiment, a suitable vector is an adeno-associated viral vector. Adeno, adeno-associated and lentiviruses are generally preferred because they infect actively dividing as well as resting and differentiated cells such as the stem cells, macrophages and neurons. A variety of adenovirus, lentivirus and AAV strains are available from the American Type Culture Collection, Manassas, Va., or available by request from a variety of commercial and institutional sources. Further, the sequences of many such strains are available from a variety of databases including, e.g., PubMed and GenBank.

In one embodiment, a lentiviral vector is used. Among useful vectors are the equine infectious anemia virus and feline as well as bovine immunodeficiency virus, and HIV-based vectors. A variety of useful lentivirus vectors, as well as the methods and manipulations for generating such vectors for use in transducing cells and expressing heterologous genes, e.g., the shRNA that inhibits the expression of Foxp1, are described in N Manjunath et al, 2009 Adv Drug Deliv Rev., 61(9): 732-745, incorporated herein by reference. In one embodiment the self-inactivating lentiviral vector (GeMCRIS 0607-793) which was successfully used to transduce T cells directed against tumor cells in leukemia patients (Porter et al., N Engl J Med. 2011 Aug. 25; 365(8):725-33) is useful to carry and express a nucleotide sequence, e.g., an shRNA, that inhibits the expression of Foxp1. See the description of one such desirable vector in Example 5 below.

In another embodiment, the vector used herein is an adenovirus vector. Such vectors can be constructed using adenovirus DNA of one or more of any of the known adenovirus serotypes. See, e.g., T. Shenk et al., *Adenoviridae: The Viruses and their Replication*", Ch. 67, in FIELD'S VIROLOGY, 6th Ed., edited by B. N Fields et al, (Lippincott Raven Publishers, Philadelphia, 1996), p. 111-2112; U.S. Pat. No. 6,083,716, which describes the genome of two chimpanzee adenoviruses; U.S. Pat. No. 7,247,472; WO 2005/1071093, etc. One of skill in the art can readily construct a suitable adenovirus vector to carry and express a nucleotide sequence as described herein, e.g., a shRNA that inhibits the expression of Foxp1, by resort to well-known publications and patents directed to such viral vectors. See, e.g., Arts, et al, 2003 Adenoviral vectors for expressing siRNAs for discovery and validation of gene function, Genome Research, 13:2325-32.

In another embodiment, the vector used herein is an adeno-associated virus vector. In another embodiment, the vector used herein is an adeno-associated virus (AAV) vector. Such vectors can be constructed using AAV DNA of one or more of the known AAV serotypes. See, e.g., U.S. Pat. No. 7,906,111 (Wilson); Gao et al, Novel Adeno-Associated Viruses From Rhesus Monkeys as Vectors for Human Gene Therapy, PNAS, vol. 99, No. 18, pp. 11854-11859, (Sep. 3, 2002); Rutledge et al, Infectious Clones and Vectors Derived from Adeno-Associated Virus (AAV) Serotypes Other Than AAV Type 2, Journal of Virology, vol. 72, pp. 309-319, (January 1998). One of skill in the art can readily construct a suitable AAV vector to carry and express a nucleotide sequence as described herein, e.g., an shRNA that inhibits the expression of Foxp1, by resort to well-known publications and patents directed to such AAV vectors. See, e.g, Grimm et al, Adeno-associated virus vectors for short hairpin RNA expression, Methods Enzymology, 392, 381-405 (2005); U.S. Pat. Nos. 7,803,611; 7,696,179.

In yet another embodiment, the vector used herein is a bacterial vector. In one embodiment, the bacterial vector is *Listeria monocytogenes*. *Listeria monocytogenes* is a food borne pathogen which has been found to be useful as a vaccine vehicle, especially in attenuated form. See, e.g., Ikonomidis et al, J. Exp. Med, 180:2209-18 (December 1994); Lauer et al, Infect. Immunity, 76(8):3742-53 (August 2008). *Listeria monocytogenes* are known to spontaneously infect dendritic cells, listerial adhesion factors internalin A and internalin B (Kolb-Mäurer et al, Infection & Immunity, 68(6):3680-8 (June 2000)). Thus, in one embodiment, the bacterial vector is live-attenuated or photochemically inactivated. The heterologous gene of interest, e.g., the shRNA the can inhibit Foxp1, such as those listed in Table 1, can be expressed recombinantly by the bacteria, e.g., via a plasmid introduced into the bacteria, or integrated into the bacterial genome, i.e., via homologous recombination.

Generally, each of these vectors also comprises a minigene. By "minigene" is meant the combination of a selected nucleotide sequence (e.g., a short nucleic acid sequence described herein or shRNA of Table 1) and the operably linked regulatory elements necessary to drive translation, transcription and/or expression of the gene product in the host cell in vivo or in vitro. As used herein, "operably linked" sequences include both expression control sequences that are contiguous with the gene of interest and expression control sequences that act in trans or at a distance to control the gene of interest.

These vectors also include conventional control elements that permits transcription, translation and/or expression of the shRNA in a cell transfected with the plasmid vector or infected with the viral vector. A great number of expression control sequences, including promoters which are native, constitutive, inducible and/or tissue-specific, are known in the art and may be utilized. In one embodiment, the promoter is an RNA polymerase promoter. In another embodiment, the promoter is an RNA polymerase promoter selected from U6, H1, T7, pol I, pol II and pol III promoters. In another embodiment, the promoter is a constitutive promoter. In another embodiment, the promoter is an inducible promoter. In one embodiment, the promoter is selected based on the chosen vector. In another embodiment, when the vector is lentivirus, the promoter is U6, H1, CMV IE gene, EF-1α, ubiquitin C, or phosphoglycero-kinase (PGK) promoter. In another embodiment, when the vector is an AAV, the promoter is an RSV, U6, or CMV promoter. In another embodiment, when the vector is an adenovirus, the promoter is RSV, U6, CMV, or H1 promoters. In another embodiment, when the vector is *Listeria monocytogenes*, the promoter is a hly or actA promoter.

Still other conventional expression control sequences include selectable markers or reporter genes, which may include sequences encoding geneticin, hygromicin, ampicillin or purimycin resistance, among others. Other components of the vector may include an origin of replication. Selection of these and other promoters and vector elements are conventional and many such sequences are available [see, e.g., Sambrook et al, and references cited therein].

These vectors are generated using the techniques and sequences provided herein, in conjunction with techniques known to those of skill in the art. Such techniques include conventional cloning techniques of cDNA such as those described in texts (Sambrook et al, Molecular Cloning: A Laboratory Manual, Cold Spring Harbor Press, Cold Spring Harbor, N.Y.), use of overlapping oligonucleotide sequences, polymerase chain reaction, and any suitable method which provides the desired nucleotide sequence.

Thus, in one embodiment, using the information taught herein and publically available and known vector construction components and techniques, one of skill in the art can construct a viral vector (or plasmid) that expresses the desired construct, e.g., a short hairpin (shRNA) sequence that suppresses the expression of Foxp1. In certain embodiments, the DNA sequence which upon expression in a vector expresses the shRNA, is selected from those reported in Table 1. See, the vector of Example 5.

In still another embodiment, the vector may be designed to co-express more than one shRNA that suppresses the expression of Foxp1, e.g., such as more than one of the sequences of Table 1.

In yet another embodiment, the vector may be designed to co-express a construct that enables targeting of the virus vector to only T cells. Such targeting will enable the virus to be employed in vivo. For example, the virus vector is designed to co-express an anti-tumor T cell receptor or a chimeric anti-tumor T cell receptor, or portion of an antibody or fragment to a T cell surface marker. Among suitable constructs for co-expression are fragments of monoclonal antibodies targeting T cell surface markers (e.g., CD3, CTLA4, CD44, CD69 or CD25), TCRs against human antigens, such as human carcinoembryonic antigen, NY-ESO-1, MAGE-A3 and MART-1, gp100 and p53. Chimeric receptors that may be co-expressed include, e.g., chimeric receptors against the antigens CD19, Epstein Barr virus, mesothelin and the folate receptor.

For example, by using the above-noted lentiviral vector (GeMCRIS 0607-793) and transductions at a multiplicity of infection of 5, a high level of expression of chimeric receptors directed against tumor cell antigens can be obtained in >85% primary human T cells (Milone et al., Molecular Therapy (2009) 17 8, 1453-1464). In one embodiment, a minigene or cassette containing a Foxp1 shRNA sequence downstream of a RNA polymerase III promoter (e.g., the H1 or the U6 promoters) could be sub cloned into the same lentiviral vector, which would therefore confer expression of the chimeric receptor and silencing of Foxp1 in the same T cell.

In still other embodiments, the viral vectors or plasmids carrying the Foxp1 shRNA are complexed or conjugated to a polymer or any other material that stabilizes the vector or assists in its targeting. Among such stabilizing polymers and materials are polyethyleneimine (PEI), which may be conjugated to the vector, resulting in the generation of nanocomplexes of about 50 nm, as described in Cubillos-Ruiz J R, et al, 2009 J. Clin. Invest., 119(8):2231-44, incorporated by reference herein. In another embodiment, such a stabilizing material is chitosan. In one embodiment, the vector is in a stable composition, with or without conjugation, with cholesterol. In another embodiment, the vector may be conjugated, to an antibody or fragment thereof that permits the vector to be preferentially targeted.

In one embodiment, the antibody is an antibody or fragment to a desirable molecule, such as a IL7 receptor. In another embodiment, the antibody is an antibody or fragment to a T cell surface marker, a T cell receptor or a chimeric receptor which also permits targeting. For example, in one another embodiment, the vectors are linked to thiolated F(ab)2 fragments of monoclonal antibodies targeting T cell surface markers (e.g., CD3, CTLA4, CD44, CD69 or CD25). In another embodiment, the antibody or fragment is to a T cell receptor or chimeric receptor such as those described above.

C. Anti-Tumor T Cells for Adoptive Transfer

To generate cells for adoptive transfer, the above-described vectors carrying the minigene expressing at least one Foxp1 shRNA, and optionally a second construct for co-expression, are delivered to an anti-tumor T cell. "Anti-tumor T cells" are primarily, but not exclusively, CD8 (cytotoxic) T cells with activity against an autologous tumor, which are able to become activated and expand in response to antigen. Anti-tumor T cells, useful for adoptive T cell transfer include, in one embodiment, peripheral blood derived T cells genetically modified with receptors that recognize and respond to tumor antigens. Such receptors are generally composed of extracellular domains comprising a single-chain antibody (scFv) specific for tumor antigen, linked to intracellular T cell signaling motifs (see, e.g., Westwood, J. A. et al, 2005, Proc. Natl. Acad. Sci., USA, 102(52):19051-19056). Other anti-tumor T cells include T cells obtained from resected tumors. In another embodiment, the T cell is a polyclonal or monoclonal tumor-reactive T cell, i.e., obtained by apheraesis, expanded ex vivo against tumor antigens presented by autologous or artificial antigen-presenting cells. In another embodiment, the T cell is engineered to express a T cell receptor of human or murine origin that recognizes a tumor antigen.

In one embodiment, T cells are designed for autologous adoptive transfer into cancer patients. The T cells are engineered ex vivo to express a shRNA capable of down-regulating FoxP1 expression once the T cells are delivered to the subject. In another embodiment, the subject's T cells can be manipulated in vivo by administration of certain therapeutic agents designed to downregulate Foxp1 activity. In one embodiment, such a therapeutic agent is a virus engineered to express the shRNA. Generally, when delivering the vector comprising the minigene by transfection to the T cells, the vector is delivered in an amount from about 5 µg to about 100 µg DNA to about $1 \times 10^4$ cells to about $1 \times 10^{13}$ cells. In another embodiment, the vector is delivered in an amount from about 10 to about 50 µg DNA to $1 \times 10^4$ cells to about $1 \times 10^{13}$ cells. In another embodiment, the vector is delivered in an amount from about 5 µg to about 100 µg DNA to about $10^5$ cells. However, the relative amounts of vector DNA to the T cells may be adjusted, taking into consideration such factors as the selected vector, the delivery method and the host cells selected. The vector may be introduced into the T cells by any means known in the art or as disclosed above, including transfection, transformation and infection. The heterologous gene of interest, e.g., the Foxp1 shRNA, may be stably integrated into the genome of the host cell, stably expressed as episomes, or expressed transiently.

In still another embodiment, the T cells are primed/pulsed with and against a selected cancer, or tumor-specific, antigen, or with and against multiple tumor antigens before transfection with the vector carrying the Foxp1 shRNA. In another example, polyclonal T cells primed against multiple tumor antigens are transduced with the above-described lentiviral vector encoding a Foxp1 shRNA sequence. These adoptive T cells are prepared by pulsing T cells with a selected cancer, or tumor-specific, antigen; transducing the pulsed T cells with a vector expressing a construct that down regulates Foxp1, and formulating said pulsed, transfected T cells with a suitable pharmaceutical carrier.

In another embodiment, the anti-tumor T cells are prepared for adoptive therapy by pulsing/priming the T cells with or against a selected cancer, or tumor-specific, antigen. The pulsed cells are then transduced with a vector expressing a TCR or chimeric anti-tumor receptor. These cells are then treated ex vivo with zinc-finger nucleases with sequences that are optimized and designed to target the unique sequence of Foxp1. By taking advantage of endogenous DNA repair machinery, these reagents remove Foxp1 from the anti-tumor T cells (lymphocytes) before adoptive transfer. The resulting T cells are prepared for adoptive therapy in a suitable pharmaceutical carrier. These T cells are prepared using techniques described in the comparable deletion of CCR5 in T cells administered to HIV infected patients in Perez et al, Nat. Biotechnol. 2008; 26:808-16, incorporated by reference herein.

Alternatively, the T cells can be transfected with multiple different viral vectors that express different Foxp1 shRNAs, and/or express TCRs and Foxp1 shRNA and/or chimeric receptors and Foxp1RNA, using the same techniques as described above.

D. Small Molecules

In still another embodiment, such a therapeutic agent is a small molecule or drug that binds to FoxP1 and inhibits its function.

The compositions comprising the small nucleic acid molecules, viruses, plasmids or T cells described above may be further associated with a pharmaceutically acceptable carrier for in vivo delivery. As used herein the term "pharmaceutically acceptable carrier" or "diluent" is intended to include any and all solvents, dispersion media, coatings, antibacterial and antifungal agents, isotonic and absorption delaying agents, and the like, compatible with administration to humans. In one embodiment, the diluent is saline or buffered saline.

II. METHODS

All of the compositions and components described above may be used in the methods described herein for stimulating anti-tumor immune activity. Thus, in one embodiment, a method of treating a cancer or enhancing an anti-tumor response in a subject having a cancer involves administering to a subject in need thereof a therapeutic reagent that down-regulates the expression of Foxp1 in T cells within the environment of the cancer cells. In one embodiment, the cancer is characterized by the presence of a solid tumor and the expression of Foxp1 is desirably down-regulated in T cells within the tumor microenvironment. These methods are particularly use for enhancing the treatment of cancer, particularly cancers that are not sensitive to other conventional treatments. In certain embodiments, the cancer is breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, leukemia, myeloma, lymphoma, glioma, or multidrug resistant cancer.

In one embodiment, the method involves administering a short nucleic acid molecule which may be a short hairpin RNA (shRNA), a short interfering RNA (siRNA), a double stranded RNA (dsRNA), a micro RNA, and an interfering DNA (DNAi) molecule to the subject or carried within the anti-tumor T cell. In one embodiment, the siRNA is delivered with a delivery agent, such as a lipid, a cationic lipid, a phospholipid, and a liposome to carry siRNA oligonucleotides targeting the expression of Foxp1. In certain embodiments, the synthetic siRNA oligonucleotide is in the form of a nanoparticle complexed with a polymer or other material as described in detail above. In one embodiment, the reagent is any of the short nucleic acid molecules of the present invention. In another embodiment, the short nucleic acid molecule is between 19 to 65 nucleotides. In yet another embodiment, the short nucleic acid molecule comprises 19-30 nucleotides that are complementary to a sequence within a full length Foxp1 nucleotide sequence SEQ ID NO: 1. In one embodiment, the short nucleic acid molecule comprises an siRNA with the sequence of SEQ ID NO: 3 or 4. In another embodiment, the short nucleic acid molecule comprises a shRNA with a sequence selected from the group consisting of SEQ ID NOs: 5, 8, 11, 14, 17, 20, 23, 26, 29, 32, 35, 38, 41, 44, 47, 50 and 53.

In another embodiment, the method provides administering a vector such as those described in detail above, which specifically infected only T cells, and which express a construct that inhibits the expression of Foxp1, in a pharmaceutically acceptable carrier or diluent. In one embodiment, where the method the use of a viral vector comprising a short nucleic acid molecule, anti-tumor T cells in the tumor environment are infected by said virus in vivo and Foxp1 is down regulated in the infected T cells. For this embodiment, the virus specifically infects only T cells. In another embodiment, a plasmid or viral vector comprises the short nucleic acid molecule, under the control of regulatory sequences. In one embodiment, the viral vector is selected from the group consisting of adenovirus or lentivirus. In another embodiment, the viral vector is complexed with a polymer. In one embodiment, the polymer is PEI, chitosan or any other material that stabilizes siRNA. In another embodiment, the method provides administering a viral vector that co-expresses an anti-tumor T cell receptor or a chimeric anti-tumor T cell receptor. Anti-tumor T cells in the tumor environment become infected by said virus in vivo and Foxp1 is down regulated in the infected T cells.

In another embodiment, the method involves adoptive T cell therapy and involves administering an anti-tumor T cell as described in detail above, e.g., a T cell transduced or transfected ex vivo with the viral vector, wherein the expression of Foxp1 in the T cell is extinguished or reduced. As described above, in one embodiment, the viral vector/plasmid is transduced ex vivo into a T cell and said T cell is introduced into the subject. In one embodiment, the construct is administered ex vivo to a T cell selected from the group consisting of (a) a polyclonal/monoclonal tumor-reactive T cell, (b) a tumor-infiltrating lymphocyte generated from aphaeresis samples or isolated from a tumor of a cancer patient, and (c) a T cell conditioned for adoptive transfer. In one embodiment, the T cell is pulsed with tumor antigen prior to transduction with the viral vector/plasmid. In another embodiment, the T cell has been conditioned for adoptive transfer by pulsing ex vivo with a tumor-specific antigen before it is transduced with the virus vector. In still another embodiment, the virus stably expresses the construct in the T cell. Expression of the construct in the T cells transduced ex vivo increases anti-tumor immunity upon administration to the subject.

Down-regulating Foxp1 in anti-tumor T cells (conditioned for adoptive transfer or not) enhances the therapeutic activity of the T cells and prolong the survival of cancer patients. The therapeutic compositions administered by these methods, e.g., whether virus, virus nanoparticle, siRNA alone, siRNA nanoparticle, anti-tumor T cell treated for adoptive therapy, are administered directly into the environment of the cancer cell or tumor microenvironment of the subject. Conventional and pharmaceutically acceptable routes of administration include, but are not limited to, systemic routes, such as intraperitoneal, intravenous, intranasal, intravenous, intramuscular, intratracheal, subcutaneous, and other parenteral routes of administration or intratumoral or intranodal administration. Routes of administration may be combined, if desired. In some embodiments, the administration is repeated periodically.

These therapeutic compositions may be administered to a patient, preferably suspended in a biologically compatible solution or pharmaceutically acceptable delivery vehicle. The various components of the compositions are prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. Other aqueous and non-aqueous isotonic sterile injection solutions and aqueous and non-aqueous sterile suspensions known to be pharmaceutically acceptable carriers and well known to those of skill in the art may be employed for this purpose.

The viral vectors or siRNA nanoparticles are administered in sufficient amounts to transduce the targeted T cells and to provide sufficient levels of gene transfer and expression to reduce or inhibit expression of Foxp1 and provide a therapeutic benefit without undue adverse or with medically acceptable physiological effects, which can be determined by those skilled in the medical arts. The adoptive T cells are similarly administered to express the Foxp1 shRNA and to reduce or inhibit expression of Foxp1 to provide a therapeutic benefit without undue adverse or with medically acceptable physiological effects, which can be determined by those skilled in the medical arts.

Dosages of these therapeutic reagents will depend primarily on factors such as the condition being treated, the age, weight and health of the patient, and may thus vary among patients. For example, a therapeutically effective adult human or veterinary dosage of the viral vector or siRNA nanoparticle is generally in the range of from about 100 μL to about 100 mL of a carrier containing concentrations of from about $1\times10^6$ to about $1\times10^{15}$ particles, about $1\times10^{11}$ to $1\times10^{13}$ particles, or about $1\times10^9$ to $1\times10^{12}$ particles virus. Methods for determining the timing of frequency (boosters) of administration will include an assessment of tumor response to the vector administration. As another example, the number of adoptively transferred anti-tumor T cells can be optimized by one of skill in the art depending upon the response and overall physical health and characteristics of the individual patient.

In one embodiment, such a dosage can range from about $10^5$ to about $10^{11}$ cells per kilogram of body weight of the subject. In another embodiment, the dosage of anti-tumor T cells is about $1.5\times10^5$ cells per kilogram of body weight. In another embodiment, the dosage of anti-tumor T cells is about $1.5\times10^6$ cells per kilogram of body weight. In another embodiment, the dosage of anti-tumor T cells is about $1.5\times10^7$ cells per kilogram of body weight. In another embodiment, the dosage of anti-tumor T cells is about $1.5\times10^8$ cells per kilogram of body weight. In another embodiment, the dosage of anti-tumor T cells is about $1.5\times10^9$ cells per kilogram of body weight. In another embodiment, the dosage of anti-tumor T cells is about $1.5\times10^{10}$ cells per kilogram of body weight. In another embodiment, the dosage of anti-tumor T cells is about $1.5\times10^{11}$ cells per kilogram of body weight. Other dosages within these specified amounts are also encompassed by these methods. See, e.g., Dudley et al, 2002, cited above; and Porter et al, 2011, cited above.

In still other embodiments, these methods of down-regulating FoxP1 are part of a combination therapy. In one embodiment, the short nucleic acid molecules, such as siRNA and shRNA, the viral vectors, and the anti-tumor T cells prepared for adoptive immunotherapy as described above, can be administered alone or in combination with various other treatments or therapies for the cancer.

In one embodiment, the methods include IL-7 treatment as tumor-specific host conditioning strategies together with Foxp1-deficient T cell transfer. IL-7Rα is one of the most critical cytokine receptors for T cell survival. The IL-7R complex is composed of IL-7Rα and the common cytokine receptor γ-chain ($γ_c$), but control of IL-7 signaling is primarily dependent on the regulation of IL-7Rα (Mazzucchelli & Durum, 2007, Nat. Rev. Immunol., 7:144-54; Jiang Q et al 2005 Cytokine Growth Factor Rev., 16:513-33). As we demonstrated, Foxp1 represses IL-7Rα expression, and Foxp1-deficient naive CD8+ T cells even proliferate in response to IL-7 directly in the absence of overt TCR stimulation. Through the administration of IL-7, we will take advantage of the higher IL-7R expression in Foxp1-deficient T cells to promote their in vivo activity, expansion and survival after adoptive transfer. Therefore, administration of IL-7 is a synergistic host conditioning strategy together with the adoptive transfer of anti-tumor Foxp1-deficient T cells. Foxp1-deficient naive T cells will show superior proliferation to IL-7, compared to wild-type activated T cells. Exogenous administration of IL-7 further promotes the in vivo activity specifically of Foxp1-deficient T cells.

Thus, in one embodiment, the method further comprises co-administering exogenous IL-7 to the subject to promote the in vivo activity of Foxp1-deficient T cells. In another embodiment, the therapeutic agent that down-regulates Foxp1, whether the siRNA, nanoparticle, virus or transduced T cells, is provided in combination with a short nucleic acid molecule that targets IL7 Receptor. This molecule can be co-expressed in the vector or in the anti-tumor T cell for adoptive therapy.

In another embodiment, the method further comprises administering to the subject along with the therapeutic agent the down-regulates Foxp1, an adjunctive anti-cancer therapy which may include a monoclonal antibody, chemotherapy, radiation therapy, a cytokine, or a combination thereof. These therapies may include co-expression of T cell receptor proteins or chimeric T cell receptor proteins in the same virus/plasmids/T cells as described above or administered to the subject in separate viruses/plasmids/T-cells.

In still another embodiment the methods herein may include co-administration or a course of therapy also using other small nucleic acid molecules or small chemical molecules or with treatments or therapeutic agents for the management and treatment of cancer. In one embodiment, a method of treatment of the invention comprises the use of one or more drug therapies under conditions suitable for said treatment.

In another embodiment of combination therapy, a passive therapeutic is administered that can immediately start eliminating the tumor. This is accompanied by administration of active immunotherapy to induce an active endogenous response to continue the tumor eradication. In one embodiment, the methods described herein include administration of the Foxp1-downregulating therapeutic compositions described above with other known cancer therapies. For example, surgical debulking, in certain embodiments is a necessary procedure for the removal of large tumor masses, and can be employed before, during or after application of the methods and compositions as described herein. Chemotherapy and radiation therapy, in other embodiments, bolster the effects of the adoptive immunotherapy described herein. Finally, immune-based therapies can eradicate residual disease and activate endogenous antitumor responses that persist in the memory compartment to prevent metastatic lesions and to control recurrences. Such combination approaches (surgery plus chemotherapy/radiation plus immunotherapy) are anticipated to be successful in the treatment of many cancers along with the methods described herein.

III. EXAMPLES

The invention is now described with reference to the following examples. These examples are provided for the purpose of illustration only. The compositions, experimental protocols and methods disclosed and/or claimed herein can be made and executed without undue experimentation in light of the present disclosure. The protocols and methods described in the examples are not considered to be limitations on the scope of the claimed invention. Rather this specification should be construed to encompass any and all variations that become evident as a result of the teaching provided herein. One of skill in the art will understand that changes or variations can be made in the disclosed embodiments of the examples, and expected similar results can be obtained. For example, the substitutions of reagents that are chemically or physiologically related for the reagents described herein are anticipated to produce the same or similar results. All such similar substitutes and modifications are apparent to those skilled in the art and fall within the scope of the invention.

Example 1: Identification of a New Mechanism of T Cell Quiescence Mediated for Foxp1

We have identified a new mechanism of T cell quiescence mediated by Foxp1, as discussed in Feng, X et al, 2011 Nature Immunol., 12:544-550, incorporated by reference herein. Our data also demonstrate that through negative regulation of IL-7 receptor α-chain (IL-7Rα) expression and T cell receptor (TCR) signaling, Foxp1 is critical in maintaining mature T cell quiescence. Correspondingly, acute deletion of Foxp1 (all four isoforms) allows mature naive CD8+ T cells to gain effector phenotypes/functions and to directly proliferate in response to IL-7.

A. Foxp1-Deficient Naive CD8+ T Cells Proliferate in Response to IL-7

To study Foxp1 function in mature T cells, we generated Foxp1f/fCre-ERT2+RosaYFP mice in which Cre recombinase becomes activated by treatment with tamoxifen and Cre induces deletion of loxP flanked Foxp1 alleles (Foxp1f/f) and the expression of yellow fluorescent protein (YFP) as a reporter. We sorted CD44loCD8+ T cells from Foxp1f/fCre-ERT2+RosaYFP mice and cultured the cells with or without tamoxifen and IL-7. Without tamoxifen, there was no YFP induction (data as shown in Feng at FIG. 1a) or cell proliferation (data not shown) in the culture by day 6. Without IL-7, most cells died in the culture (data not shown).

In contrast, in cultures with tamoxifen and IL-7, YFP+ cells started to emerge around day 2 (data not shown). By day 6, in contrast to YFP– cells, most YFP+ cells proliferated, upregulated their expression of CD44 and CD25, slightly downregulated CD62L and increased in size (data as shown in Feng at FIG. 1b). We also observed such phenotypic changes, although to a lesser extent, in nondividing YFP+ cells (data as shown in Feng at FIG. 1b). We also examined CD44loCD8+ T cells sorted from Foxp1f/+Cre-ERT2+RosaYFP mice.

Consistent with published observations of only a minor phenotype for CD8+ T cells from Foxp1f/+Cd4-Cre mice (which have one loxPflanked Foxp1 allele and expression of Cre driven by Cd4)33, YFP+Foxp1f/+Cre-ERT2+RosaYFP CD8+ T cells still expressed Foxp1 and did not proliferate or change their phenotype (data not shown). This indicated that complete deletion of Foxp1 in CD8+ T cells was required for the phenotypic changes we observed. These changes occurred by day 6 only in cultures treated with IL-7, but not in those treated with IL-4 (or IL-15; data as shown in Feng at FIG. 1b and data not shown), although there was equally efficient deletion of Foxp1 and induction of YFP+ cells in all cultures by day 4 (data not shown).

Functional analysis showed that stimulation with phorbol 12-myristate 13-acetate (PMA) plus ionomycin induced a greater frequency of IFN-γ- and IL-2-producing YFP+ cells than IFN-γ- and IL-2-producing YFP− T cells (data as shown in Feng at FIG. 1c). We also observed such functional changes in nondividing YFP+ cells (data as shown in Feng at FIG. 1c), which indicated that both the phenotypic changes and functional changes in YFP+ cells were induced without proliferation. The proliferation of YFP+ cells in response to IL-7 was not due to contamination by CD44hiCD8+ T cells during the sorting of CD44loCD8+ T cells from the mice, because YFP+ cells from cultures of CD44loCD8+ T cells proliferated much more than did YFP− cells from cultures of sorted CD44hiCD8+ T cells (data as shown in Feng at FIG. 1b,d). YFP+ cells from cultures of sorted CD44hiCD8+ T cells also proliferated substantially and upregulated CD25 expression (data as shown in Feng at FIG. 1d).

To further confirm that Foxp1-deficient naive CD8+ T cells proliferated in response to IL-7, we sorted CD44loCD8+ T cells from Foxp1f/fCre-ERT2+RosaYFP mice and control wild-type littermates (Foxp1f/fRosaYFP mice) and cultured them for 2 d, then sorted YFP+ and wild-type control cells and cultured them in equal numbers with IL-7 alone. Because we noted deletion of Foxp1 in some YFP− T cells from Foxp1f/fCre-ERT2+RosaYFP mice after tamoxifen treatment (data not shown), we used cultured wild-type T cells as controls in this set of experiments (for the same reason, we used congenic wild-type controls in the in vivo transfer experiments described below). By day 6, YFP+ cells proliferated more, which resulted in more total cells and higher granzyme B expression than that of wild-type control cells (data not shown). These results suggest that the deletion of Foxp1 leads mature naive CD8+ T cells to gain both effector phenotype and function and proliferate in response to IL-7 in the absence of overt TCR stimulation. Mature naive CD4+ T cells in which Foxp1 was acutely deleted gained effector phenotype and function as well (albeit to a much lesser extent than did CD8+ T cells) but did not proliferate in response to IL-7 or IL-4 in vitro (data not shown).

B. Foxp1 Regulates T Cell Quiescence and Homeostasis In Vivo

To examine how Foxp1 regulates naive T cell quiescence and homeostasis in vivo, and to avoid potential secondary effects due to the deletion of Foxp1 in non-T cells after tamoxifen treatment in vivo, we used an adoptive-transfer model system. We mixed CD44lo CD8+ or CD4+ T cells sorted from Foxp1f/fCre-ERT2+RosaYFP and control CD45.1+ congenic wild-type mice and labeled the cells with the fluorescent dye CellTrace, then transferred them together into intact recipient mice, which received tamoxifen treatment 1 d before the transfer and for the first 3 d after transfer. At 8 d after transfer, most of the YFP+ cells in the recipient mice up regulated their expression of IL-7Rα and CD44 but did not proliferate (data as shown in Feng at FIG. 6a and data not shown). A higher percentage of YFP+ cells than wild-type control cells produced IFN-γ and/or IL-2 after stimulation with PMA plus ionomycin (data as shown in Feng at FIG. 6b).

At 15 d after transfer, the deletion of Foxp1 induced the proliferation of a substantial fraction of CD8+ and CD4+ T cells (data as shown in Feng at FIG. 6c). In recipient mice that did not receive any tamoxifen treatment, we detected no proliferation of either Foxp1f/fCre-ERT2+RosaYFP T cells or wild-type control T cells at 15 d after transfer (data not shown). These results suggest that Foxp1 is critical for the maintenance of quiescence in both naive CD8+ and CD4+ T cells in lympho-replete mice. The proliferation of Foxp1-deficient naive CD8+ T cells in response to IL-7 in vitro occurred without TCR stimulation (data as shown in Feng at FIG. 1).

To determine whether TCR engagement is important for the regulation of naive T cell quiescence and homeostasis by Foxp1 in vivo, we mixed CD44loCD8+ T cells sorted from Foxp1f/fCre-ERT2+RosaYFP and control CD45.1+ congenic wild-type mice, labeled the cells with CellTrace reagent and cultured them for 2 d with tamoxifen in medium. These conditions ensured deletion of Foxp1 before the transfer of cells and subsequent proliferation in the lymphopenic environment of sublethally irradiated mice deficient in H-2Kb and H-2Db. At 7 d after transfer, whereas most of the wild-type control cells did not proliferate, many more Foxp1-deficient naive CD8+ T cells proliferated and upregulated CD44 expression in recipient mice deficient in H-2Kb and H-2Db (data as shown in Feng at FIG. 7a,b).

We obtained similar results in parallel experiments in which we first transferred cells into irradiated mice deficient in H-2Kb and H-2Db, then treated the recipient mice with tamoxifen in vivo (data not shown).

However, in recipient mice deficient in recombination-activating gene 1, Foxp1-deficient CD8+ T cells proliferated only slightly more than wild-type control cells did (data not shown), which indicated that the enhanced proliferation of Foxp1-deficient CD8+ T cells in lymphopenia was less notable when complexes of self peptide and major histocompatibility complex were available. Nevertheless, inhibition of IL-7R signaling with antibody to IL-7 and antibody to IL-7R almost completely blocked the proliferation of Foxp1-deficient CD8+ T cells in recipient mice deficient in H-2Kb and H-2Db (data as shown in Feng at FIG. 7c). These results suggest that in lymphopenic conditions and in the absence of (or in the presence of considerably less) engagement of the TCR with complexes of self peptide and major histocompatibility complex, Foxp1 is essential for naive T cell quiescence and homeostasis and that this regulation is dependent on IL-7-IL-7R.

We have provided direct evidence that Foxp1 has an indispensable role in maintaining naïve T cell quiescence, in part by repressing IL-7Rα expression. That view was supported by the following results: Foxp1-deficient naive CD8+ T cells gained effector phenotype and function in response to IL-7 but not in response to IL-4, and the amount of IL-7R was critical for the proliferation of Foxp1-deficient CD8+ T cells in response to IL-7 in vitro. In addition, Foxp1-deficient naive CD8+ T cells proliferated in vivo in lymphopenic mice deficient in H-2Kb and H-2Db in an IL-7-dependent manner.

Here we have shown that Foxp1 is a repressor of IL-7Rα expression. It also seemed that Foxp1 and Foxo1 had the ability to bind to the same predicted forkhead-binding site in the Il7r enhancer region, which suggests that these two transcription factors may compete for the binding and antagonize each other to regulate IL-7Rα expression in T cells. The finding that down regulation of IL-7Rα expression in the absence of Foxo1 was Foxp1 dependent indicates a potential role of Foxp1 in regulating Foxo1 function.

Foxp1 and Foxo1 have been shown to upregulate the expression of recombination-activating genes during early B cell development by binding to the same 'Erag' enhancer region. However, neither transcription factor seems to regulate these genes in T lineage cell development. Foxo1 affects IL-7Rα expression in early B lineage cells, but deletion of Foxp1 does not affect IL-7Rα expression in pro-B cells. These results suggest that Foxp1 and Foxo1 may interact in complex and distinct ways in different parts of the immune system.

In addition to regulating IL-7Rα expression, Foxp1 seems to control other molecules critical for regulating T cell quiescence. Our results have shown that Foxp1 negatively regulates the MEK-Erk pathway. Transgenic mice expressing the oncogenic protein K-Ras develop T cell lymphoma and/or leukemia characterized by aberrantly high CD44 expression in thymocytes, which is consistent with the activated phenotype of Foxp1-deficient thymocytes.

We attempted to introduce a dominant negative K-Ras to inhibit MEK-Erk signaling and determine whether it could restore the activated phenotype of Foxp1-deficient T cells in Foxp1f/fCd4-Cre mice. However, the dominant negative K-Ras almost completely blocked T cell development (data not shown). Nonetheless, we found that blocking MEK-Erk activation impaired the proliferation of Foxp1-deficient naive CD8+ T cells in response to IL-7 in vitro. It has been shown that the MEK-Erk pathway can be regulated by IL-7R and signaling pathways other than TCR signaling. Because Foxp1-deficient CD8+ T cells in which IL-7Rα expression was adjusted to nearly wild-type amounts still proliferated in response to IL-7 (whereas wild-type CD8+ T cells did not), blocking MEK-Erk activation probably inhibits pathways regulated by Foxp1, but independently of IL-7R-signaling. It has been proposed that constitutive low-intensity TCR signaling, independently of receptor ligation, has an important role in T cell development, and low Erk kinase activity is part of the TCR basal signaling. Therefore, although the proliferation of Foxp1-deficient naive CD8+ T cells in response to IL-7 in vitro and in lymphopenic mice deficient in H-2Kb and H-2Db in vivo would indicate that there is no obvious TCR engagement, Foxp1 may regulate a basal TCR signal involving MEK-Erk activity.

It is possible that in the absence of Foxp1, the integration of both enhanced IL-7R and basal TCR signals act together to drive the naïve T cells to proliferate. The nature and role of basal TCR signaling in mature T cells remain unknown. Further studies are needed to address how MEK-Erk signaling is involved in the Foxp1 regulation of T cell quiescence in the absence of overt TCR stimulation.

Naive CD4+ T cells with acute deletion of Foxp1 did not proliferate in response to IL-7 in vitro. Although the underlying mechanism is not clear, this observation is consistent with published reports showing that CD8+ T cells are more responsive to IL-7 than CD4+ T cells in in vitro cultures9. Nevertheless, we have shown that naive CD4+ T cells in which Foxp1 was acutely deleted had proliferation in intact recipient mice similar to that of Foxp1-deficient naive CD8+ T cells, which indicates that Foxp1 controls T cell quiescence in both CD4+ and CD8+ T cells in vivo.

In summary, our results have shown that Foxp1 exerts essential cell-intrinsic transcriptional regulation on the quiescence and homeostasis of naive T cells by negatively regulating IL-7Rα expression and MEK-Erk signaling. Our findings have demonstrated coordinated regulation that actively inhibits T cell activation signals and indicate that lymphocyte quiescence does not occur by default but is actively maintained.

Example 2: Wild-Type Tumor-Associated T Cells Up-Regulate Foxp1 mRNA as Tumor Progresses In addition, we have demonstrated that tumor-associated T cells up-regulate Foxp1 mRNA as tumor progresses in preclinical models of established ovarian carcinoma.

Foxp1 mRNA was quantified by real-time PCR in adoptively transferred $CD3^+CD8^+$ T cells sorted from tumor locations at different temporal points after ID8-Vegf/Defb29 tumor challenge. Adoptively transferred effector T cells represent naïve T cells primed for 7 days against tumor antigen in vitro (Cancer Res. 2009; 69: 6331-8). These T cells were FACS-sorted from peritoneal wash samples based on the expression of a "congenic" marker (CD45.1), which is not expressed by endogenous (non-transferred, CD45.2) T cells. Relative mRNA expression was standardized by GAPDH mRNA.

Immersed in ovarian tumor masses, it is likely that the potential repeated tumor antigen stimulation, plus the presence of regulatory dendritic cells (DCs) and alternatively polarized macrophages presenting antigens in the context of suboptimal levels of co-stimulatory molecules, all promote sustained expression of high levels of Foxp1 (particularly Foxp1D), which we have shown to dampen T cell responses. The results are shown in the graph of FIG. 1B.

Example 3: Tumor-Reactive Foxp1-Deficient T Cells Exert Superior Therapeutic Effects Compared to Wild-Type T Cells To further determine the role of Foxp1, we treated a preclinical mouse model of established ovarian carcinoma, i.e., ID8-Defb29/Vegf-a ovarian carcinoma bearing mice, as described in Conejo-Garcia J R, et al, 2004 Nat Med, 10(9):950-8 and Cubillos-Ruiz J R, et al, 2009 J. Clin. Invest., 119(8):2231-44). In this study, mice express a congenic marker (CD45.1), to allow distinguishing adoptively transferred from endogenous T cells in subsequent experiments.

Anti-tumor T cells were negatively immune purified from the spleens of naïve (non tumor-bearing) mice, which were either Foxp1-deficient ($Foxp1^{f/f}$) or wild-type ($Foxp1^{f/+}$). These mice strains are generated as described in Feng, X et al, 2010 Blood, 115(3):510-518, incorporated herein by reference. Both classes of T cells were then primed for 7 days against tumor antigens derived from resected ovarian tumors of the mouse model, as described in Nesbeth, Y. C. et al. 2010 J Immunol 184, 5654-62, incorporated by reference.

The mice were allowed to grow under normal conditions for 23 days in which they developed (advanced) orthotopic ovarian cancer. At day 23, either the Foxp1-deficient T cells or wild type T cells (both of them expressing CD45.2) were adoptively transferred into separate groups of mice at $10^6$ anti-tumor T cells/mouse by ip injection.

Peritoneal wash samples were taken from the mice at day 3 and day 7 post adoptive transfer and examined by FACS. FACS analysis (not shown) was performed of T cell types in a serum sample subjected to flow cytometry on day 3 and day 7 following the adoptive transfer to the ID8-Defb29/Vegf-a mouse model of ovarian cancer of Foxp1-deficient T cells, showing gating on CD3+ and using a CD45.2 marker, CD8+ marker and CD4+ marker. The results are shown in Table 2 below.

TABLE 2

| Day | Cell Type | Foxp1KO T cell Transfer | WT Control T cell Transfer |
|---|---|---|---|
| 3 | # $CD45.2^+$ T cells | 18876 | 38980 |
|   | % Total T cells | 6.92% | 6.57% |

TABLE 2-continued

| Day | Cell Type | Foxp1KO T cell Transfer | WT Control T cell Transfer |
|---|---|---|---|
|   | # CD8+ T cells/% CD45.2+ T cells | 5895/31.2% | 7560/19.4% |
|   | # CD4+ T cells/% CD45.2+ T cells | 12095/64.1% | 29629/76% |
| 7 | # CD45.2+ T cells | 5656 | 10450 |
|   | % Total T cells | 0.996% | 1.11% |
|   | # CD8+ T cells/% CD45.2+ T cells | 4522/80% | 1636/15.7% |
|   | # CD4+ T cells/% CD45.2+ T cells | 666/11.8% | 8592/82.2% |

The FACS analysis of adoptively transferred lymphocytes at tumor (peritoneal) locations showed that adoptive cell transfer of Foxp1-deficient T cells in the mice with ovarian cancer produced a significant increase in survival of CD8+ lymphocytes (cytotoxic effector T cells) after 3 and 7 days over that seen when the mice were administered wild-type T cells. Therefore, Foxp1-deficient tumor-reactive T cells are superior to resist tumor-induced immunosuppressive signals and elicit enhanced anti-tumor immunity.

Figure 1B:
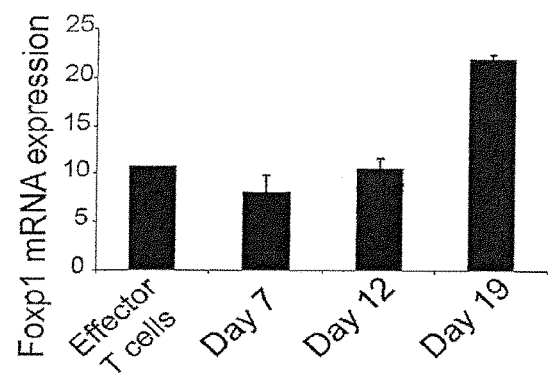
FIG. 1B is a bar graph showing the tumor associated CTLs up-regulate Fox-1p during tumor progression, as discussed in Example 2.

As shown in FIG. 1A, the administration of wild-type tumor-reactive T cells induced some modest but significant survival increase in the absence of any host conditioning intervention. In contrast (data not shown), adoptive administration of anti-tumor Foxp1-deficient T cells stopped ovarian cancer progression, so that all treated mice do not show any signs of disease 6 days after the last mouse treated with control wild-type T cells died.

Example 4: Generation of siRNA and shRNA

A. Design of an siRNA

The design of suitable siRNA involves the design of the siRNA with 21, 23, or 27 nucleotides for modulation of Foxp1, without chemical modification. The Foxp1 target gene SEQ ID NO: 1 is screened for accessible sites and siRNA is synthesized considering the open reading frame (ORF) sequences of Foxp1.

The following general requirements are considered in siRNA design:
a. No runs of four or more A, T, G, or U in a row.
b. The following sequences are avoided, as they can induce an interferon response. A) 5'-UGUGU-3' and B) 5'-GUCCUUCAA-3'
c. The first 200 bases are omitted from the start codon to avoid binding to regulatory element of SEQ ID NO: 1.
d. Each siRNA duplex is checked in silico to avoid silencing of off-target effects made on BLAST search considering the following parameters:
  I. Low complexity filtering is removed to avoid insignificance by BLAST resulting in limited or no query sequencer.
  II. The word size was set to 7 letters, the minimal value algorithm
  III. Expected value threshold is set at 1000 to avoid the probability of short sequence occurrence.
    siRNA synthesis is performed by commercially available methods (e.g., Qiagen) using chemically-protected phosphoramidite monomers. Resultant oligomers are purified by PAGE, desalting, or IE-HPLC. The quality of each siRNA is analyzed by MALDI-TOF and yields are determined by an integrated spectrophotometer.

One embodiment of an siRNA for Foxp1 has the sequence:

SEQ ID NO: 3
AAUCUGGGACUGAGACAAA.

Another embodiment of an siRNA for Foxp1 has the sequence:

SEQ ID NO: 4
GAUGCAAGAAUCUGGGACU.

B. Design of an siRNA Nanoparticle

The siRNA in one embodiment is conjugated with PEI by conventional methods, for example as described in Cubillos-Ruiz et al, J. Clin. Invest., 119(8):2231-44 (August 2009) which is incorporated by reference herein.

C. Design of an shRNA

The shRNA is based upon the siRNA sequence above or the ORF of Gene ID: 27086 (see SEQ ID NOs: 1 and 2). Using commercial available methods, the shRNA is designed by synthesizing the siRNA sequence above, followed by a 9-15 nt loop sequence, and further followed by a reverse complement of the siRNA sequence. For examples, see, e.g., the DNA sequences that are used to express in vectors the shRNAs recited in Table 1.

Example 5: Designing a Virus Containing a Foxp1 shRNA and Preparation of Anti-Tumor T Cells To achieve Foxp1 knock-down in a therapeutic setting in humans, we use Foxp1 shRNA-containing Lentivirus that are currently being used in clinical trials for gene therapy. For example, we use a self-inactivating lentiviral vector (GeMCRIS 0607-793) which was successfully used to transduce T cells directed against tumor cells in leukemia patients (Porter et al., N Engl J Med. 2011 Aug. 25; 365(8):725-33). By using this lentiviral vector and transductions at a multiplicity of infection of 5, a high level of expression of chimeric receptors directed against tumor cell antigens can be obtained in >85% primary human T cells (Milone et al., Molecular Therapy (2009) 17(8), 1453-64).

A cassette containing a Foxp1 shRNA sequence downstream of a RNA polymerase III promoter (e.g., the H1 or the U6 promoter) is subcloned into pRRL-SIN-CMV-eGFP-WPRE, a third generation, self-inactivating lentiviral vector plasmid, replacing the CMV promoter. The presence of this single construct confers expression of the chimeric receptor and silencing of Foxp1 in the same T cell. Alternatively, different viral vectors are used to express chimeric receptors and shRNA. In another experiment, polyclonal T cells primed against multiple tumor antigens are transduced only with this lentiviral vector encoding a Foxp1 shRNA sequence. The Foxp1 shRNA sequences that are used are listed in Table 1.

Thereafter we infect purified human T lymphocytes and examine the expression levels of Foxp1 by western blotting. The cells that achieve efficient Foxp1 knock-down are used later in a therapeutic setting.

Example 6: T Cell Mediated Immunotherapy in an Ovarian Cancer Model

Mice: Female B6.Ly5.2 (congenic, CD45.1+) mice were received from National Cancer Institute. Foxp1$^{f/f}$CD4-Cre (Foxp1 KO) and control Foxp1$^{+/+}$ (Control Foxp1$^{+/+}$) mice in CD45.2+ background were bred in the animal facility of the Wistar Institute, Philadelphia. All experiments were performed in accordance with the protocols approved by Institutional Animal Care and User Committee of the Wistar Institute.

Ovarian Tumor Model: We initially used transplantable ID8 mice model for ovarian cancer. Preliminary experiments utilize modification of ID8, ID8-Vegf/Defb29 which is more aggressive and recapitulates the microenvironment of human solid ovarian tumors. Moreover, compared to the parental ID8 model, immune rejection of established ID8-Vegf/Defb29 tumors are not yet reported.

Generation of ovarian tumors in mice: On day 0 of the experiments, $2\times10^6$ ID8-Vegf/Defb29 cells were intraperitoneally inoculated into 6-7 week old female mice.

Example 7: In Vitro Priming of Foxp1 KO and Control Foxp1$^{+/+}$ T Cells for Immunotherapy A. Generation of Murine Bone Marrow Derived Dendritic Cells (BMDCs) for In Vitro T Cell Priming.

BMDCs were generated from bone marrow (BM) collected from tibia and femur of 6-8 week old female C57Bl/6 mice. $2\times10^6$ BM cells were cultured in 10 ml RPMI1640 medium supplemented with 10% heat inactivated fetal bovine serum, penicillin/streptamicine, 50 mM 2-mercaptoethanol, L-Glutamine and sodium pyruvate (R10 medium) and 10 ng/ml recombinant mouse granulocyte/macrophage-colony stimulating factor (GM-CSF) (Peprotech). Half-medium changes were carried out every two days. On day 7, approximately 80% of the cells in culture were CD11c+ dendritic cells.

B. Irradiation of ID8-Vegf/Defb29 Cells:

ID8-Vegf/Defb29 cells were g-irradiated for 10000 rads using a Mark 1 irradiator (J. L. Shepherd & Associates, Glendale, Calif.). Cells were then UV irradiated for 30 minutes.

C. Tumor Antigen Pulsing of BMDCs:

On day 7 of the culture, BMDCs were collected by vigorous pipetting. BMDCs were then cultured over night with irradiated ID8-Vegf/Defb29 cells at 10:1 ratio in complete R10 medium. Tumor antigen pulsed BMDCs were recovered on next day for T cell priming.

D. Isolation and In Vitro Priming of Foxp1 KO and Control Foxp1$^{+/+}$ T Cells:

T cells were isolated from the spleen and lymph nodes of Foxp1 KO and control Foxp1$^{+/+}$ mice using Militenyi mouse Pan T cell isolation kit. Isolated T cells were cultured for 7 days with tumor antigen pulsed BMDCs at 10:1 ratio in R10 medium supplemented with 50 U/ml IL-2 in a 12 well tissue culture plate at a density of $2\times10^6$ cells/well.

Example 8: T Cell Immunotherapy with Antigen Primed Foxp1 KO T Cells

On day 7, primed T cells were recovered, and washed with PBS. $1\times10^6$ primed T cells were intraperitoneally transferred into day 24 ID8-Vegf/Defb29 tumor bearing mice (see Example 6). Control mice received either primed control Foxp1$^{+/+}$ T cells or PBS.

Follow cytometry analysis for cell number and viability: On day 3 and 6 of T cell adoptive transfer, two mice each from the Foxp1 KO, control Foxp1$^{+/+}$ T cell transferred or PBS treated groups were sacrificed. A peritoneal wash is preformed to collect cells. Spleens and BM were also collected. RBC was lysed followed by incubation with anti-CD16/CD32 antibody to block nonspecific FcR binding. Cells were stained with CD45.2 (congenic marker), CD4, CD8, CD3e, CD45, 7AAD (viability marker), Annex-inV (apoptosis marker) and analyzed using Becton Dickinson (BD) LSR. Data were processed using FlowJo software.

Survival: ID8-Vegf/Defb29 tumor bearing mice received T cell immunotherapy or the control PBS on day 24 were closely monitored for survival.

Example 9: Use of siRNA and shRNA in Mouse Model of Ovarian Cancer

A. Use of shRNA

About $10^6$ cells/mouse of the T cells of Example 5 are administered to mice of the ovarian cancer model of Example 6 by intraperitoneal injection. Controls are wild-type T cell-injected mice. In different groups of treated mice, samples of the blood and peritoneal wash of each mouse are assayed by FACS after 3, 7 and 21 days. The adoptive T cell therapy using T cells transduced with a lentivirus expressing this shRNA is able to inhibit tumor growth and cause tumor regression in this animal model. Therefore the present compositions and methods are suitable and effective for therapy of cancer and proliferative disease.

B. Use of siRNA

About 50 μg/injection of the siRNA/siRNA nanoparticle described above was administered to mice of the ovarian cancer model of Example 2 by intraperitoneal injection. Controls are PBS-injected mice. In different groups of treated mice, samples of the blood and peritoneal wash of each mouse is assayed by FACS after 3, 7 and 21 days. A significant increase in survival was observed.

The siRNA composition is able to inhibit tumor growth and cause tumor regression in these animal models. Therefore the present compositions and methods are suitable and effective for therapy of cancer and proliferative diseases.

Example 10: Foxp1 is Up-Regulated in Tumor-Reactive T Cells in the Tumor Microenvironment Naïve, negatively immunopurified T cell splenocytes were primed against tumor antigen for 7 days by incubation with bone marrow-derived dendritic cells pulsed with double (UV+gamma) irradiated tumor cells (FIG. 2, lanes 1 and 3; Day 6 effectors). Tumor antigen-primed T cells were then administered to CD45.1 (congenic) advanced ID8-Defb29/VEGFα tumor-bearing mice. Mice were sacrificed 2 days later and adoptively transferred (CD45.2+) CD8 and CD4 T cells were FACS-sorted from peritoneal wash samples (FIG. 2, lanes 2 and 5; Day 2 after transfer), along with endogenous (host-derived, CD45.1) tumor-associated T cells (FIG. 2, lanes 3 and 6). Foxp1 was quantified in all samples by Western-blot.

Example 11: Foxp1 T Cells are Resistant to the Abrogation of T Cell Expansion Induced by TGFβ

Naïve, negatively immunopurified CD8 and CD4 T cell splenocytes (from both wild-type and Foxp1 KO mice) were CFSE-labeled and expanded in the presence of CD3/CD28 Ab-coated beads (Invitrogen). When indicated, 5 ng/mL of TGFb was added, and CFSE dilution (indicative of T cell proliferation) was monitored by flow cytometry. The results of abrogation of T cell expansion induced by TFGβ are shown by contrasting FIG. 3A with 3C and 3B with 3D.

Example 12: TGFβ Repress cJun Activation in Wt but not in Foxp1 KO Cd8+ T Cells Naïve, negatively immunopurified CD8 T cell splenocytes (from both wild-type and Foxp1 KO mice) were stimulated in the presence of CD3/CD28 Ab-coated beads (Invitrogen). When indicated, 5 ng/mL of TGFb was added to the wells, and both total and phosphorylated c-Jun were analyzed by Western-blot. Note the induction of c-Jun phosphorylation upon CD3/CD28 activation and how it is selectively abrogated in wild-type T cells in the presence of TGFβ.

Examples 10-12 show that the Foxp1 and TGFβ pathways converge, so that Foxp1 is required for the tolerogenic effect induced by TGFβ in the microenvironment of virtually all solid tumors. Correspondingly, Foxp1-deficient tumor reactive T cells are insensitive to this immunosuppressive mechanism, and therefore exert superior antitumor protection. In addition, Foxp1 is upregulated in T cells in the tumor microenvironment at the protein level, pointing to a mechanism of tumor-induced immunosuppression.

Each and every patent, patent application including U.S. patent application Ser. No. 14/350,588, International Patent Application No. PCT/US2012/061556, and U.S. Provisional patent application No. 61/552,630, and publication, including publications listed herein, and publically available peptide sequences cited throughout the disclosure, as well as the Sequence Listing, is expressly incorporated herein by reference in its entirety. Embodiments and variations of this invention other than those specifically disclosed above may be devised by others skilled in the art without departing from the true spirit and scope of the invention. The appended claims include such embodiments and equivalent variations.

The invention claimed is:

1. A composition for treating a cancer comprising a T cell pulsed ex vivo with a selected cancer-specific antigen or tumor-specific antigen, the T cell having therein a vector expressing a short hairpin RNA (shRNA) construct that down regulates or extinguishes Foxp1, the shRNA under the control of a suitable promoter, which composition is in a pharmaceutically acceptable carrier or diluent that is suitable for administration to a human subject, wherein the shRNA is expressed in the vector by a DNA sequence of SEQ ID NO: 5.

2. The composition according to claim 1, wherein the vector is a viral vector selected from the group of lentiviral, adenoviral or retroviral vectors.

3. The composition according to claim 1, wherein said antigen is from a cancer or tumor which is selected from the group consisting of breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, leukemia, myeloma, lymphoma, glioma, and multidrug resistant cancer.

4. The composition according to claim 2, wherein the shRNA containing vector is a lentiviral vector and the promoter is an RNA polymerase III promoter.

5. A composition for treating a cancer comprising a T cell pulsed ex vivo with a selected cancer-specific antigen or tumor-specific antigen, the T cell and having therein a vector expressing a short hairpin RNA (shRNA) construct that down regulates or extinguishes Foxp1, the shRNA construct under the control of a suitable promoter, which composition is in a pharmaceutically acceptable carrier or diluent that is suitable for administration to a human subject, wherein the shRNA is expressed in the vector by a DNA sequence of SEQ ID NO: 8, 11 or 14.

6. The composition according to claim 5, wherein the vector is a viral vector selected from the group of lentiviral, adenoviral or retroviral vectors.

7. The composition according to claim 5, wherein said antigen is from a cancer or tumor which is selected from the group consisting of breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, leukemia, myeloma, lymphoma, glioma, and multidrug resistant cancer.

8. The composition according to claim 5, wherein the shRNA containing vector is a lentiviral vector and the promoter is an RNA polymerase III promoter.

* * * * *

```
                       SEQUENCE LISTING

<160> NUMBER OF SEQ ID NOS: 55

<210> SEQ ID NO 1
<211> LENGTH: 7102
<212> TYPE: DNA
<213> ORGANISM: Homo sapiens
<220> FEATURE:
<221> NAME/KEY: CDS
<222> LOCATION: (527)..(2560)

<400> SEQUENCE: 1 gggggtggg cgccagcgcc ccggcgaacg gcaaagaggg agccgctccc gctcgggggg        60
ccgctggagt gcccagcggg aacccgaaag tttgtaagag gaagagagcg cgcggcgagc      120
gagcgagcgg gccggggca gcggcagcgg cgccggggac catggtgctg ccggcgcctc       180
ctccgcgggc gtgaaggcgg cgctcctact ccctccccgg actccgcggt gtcccagaag      240
cttttgttga caattccagt ttccgaacaa aacatttcgg caatggtgag ggcttcgatc      300
ccttctctga tttgctgtca gccatgaacg gatggatgtg atgcctgcta gccaaaaggc      360
ttccctctgt gtgttgcagt cctgtggcat tatgcatgcc ccctcccagt gaccccaggc      420
tttttatggc tgtgagacac gttaaaattt caggggtaag acgtgacctt ttgaggtgac      480
tataactgaa gattgcttta cagaagccaa aaaaggtttt tgagtc atg atg caa        535
                                                    Met Met Gln
                                                    1 gaa tct ggg act gag aca aaa agt aac ggt tca gcc atc cag aat ggg        583
Glu Ser Gly Thr Glu Thr Lys Ser Asn Gly Ser Ala Ile Gln Asn Gly
    5                  10                  15 tcg ggc ggc agc aac cac tta cta gag tgc ggc ggt ctt cgg gag ggg        631
Ser Gly Gly Ser Asn His Leu Leu Glu Cys Gly Gly Leu Arg Glu Gly
20                  25                  30                  35 cgg tcc aac gga gag acg ccg gcc gtg gac atc ggg gca gct gac ctc        679
Arg Ser Asn Gly Glu Thr Pro Ala Val Asp Ile Gly Ala Ala Asp Leu
                40                  45                  50 gcc cac gcc cag cag cag cag caa cag gca ctt cag gtg gca aga cag        727
Ala His Ala Gln Gln Gln Gln Gln Ala Leu Gln Val Ala Arg Gln
                55                  60                  65 ctc ctt ctt cag cag caa cag cag caa gtt agt gga tta aaa tct            775
Leu Leu Leu Gln Gln Gln Gln Gln Gln Val Ser Gly Leu Lys Ser
        70                  75                  80 ccc aag agg aat gac aaa caa cca gct ctt cag gtt ccc gtg tca gtg        823
Pro Lys Arg Asn Asp Lys Gln Pro Ala Leu Gln Val Pro Val Ser Val
    85                  90                  95
```

-continued

| | | |
|---|---|---|
| gct atg atg aca cct caa gtt atc act ccc cag caa atg cag cag atc<br>Ala Met Met Thr Pro Gln Val Ile Thr Pro Gln Gln Met Gln Gln Ile<br>100                         105                      110                  115 | 871 |
| ctc cag caa caa gtg ctg agc cct cag cag ctc cag gtt ctc ctc cag<br>Leu Gln Gln Gln Val Leu Ser Pro Gln Gln Leu Gln Val Leu Leu Gln<br>                    120                      125                      130 | 919 |
| cag cag cag gcc ctc atg ctt caa cag cag ctt caa gag ttt tat<br>Gln Gln Gln Ala Leu Met Leu Gln Gln Gln Leu Gln Glu Phe Tyr<br>                135                      140                      145 | 967 |
| aaa aaa caa cag gaa cag ttg cag ctt caa ctt tta caa caa caa cat<br>Lys Lys Gln Gln Glu Gln Leu Gln Leu Gln Leu Leu Gln Gln Gln His<br>                150                      155                      160 | 1015 |
| gct gga aaa cag cct aaa gag caa cag cag gtg gct acc cag cag ttg<br>Ala Gly Lys Gln Pro Lys Glu Gln Gln Gln Val Ala Thr Gln Gln Leu<br>165                         170                      175 | 1063 |
| gct ttt cag cag cag ctt tta cag atg cag cag tta cag cag cag cac<br>Ala Phe Gln Gln Gln Leu Leu Gln Met Gln Gln Leu Gln Gln Gln His<br>180                         185                      190                      195 | 1111 |
| ctc ctg tct ttg cag cgc caa ggc ctt ctg aca att cag ccc ggg cag<br>Leu Leu Ser Leu Gln Arg Gln Gly Leu Leu Thr Ile Gln Pro Gly Gln<br>                    200                      205                      210 | 1159 |
| cct gcc ctt ccc ctt caa cct ctt gct caa ggc atg att cca aca gaa<br>Pro Ala Leu Pro Leu Gln Pro Leu Ala Gln Gly Met Ile Pro Thr Glu<br>                215                      220                      225 | 1207 |
| ctg cag cag ctc tgg aaa gaa gtg aca agt gct cat act gca gaa gaa<br>Leu Gln Gln Leu Trp Lys Glu Val Thr Ser Ala His Thr Ala Glu Glu<br>                    230                      235                      240 | 1255 |
| acc aca ggc aac aat cac agc agt ttg gat ctg acc acg aca tgt gtc<br>Thr Thr Gly Asn Asn His Ser Ser Leu Asp Leu Thr Thr Thr Cys Val<br>245                         250                      255 | 1303 |
| tcc tcc tct gca cct tcc aag acc tcc tta ata atg aac cca cat gcc<br>Ser Ser Ser Ala Pro Ser Lys Thr Ser Leu Ile Met Asn Pro His Ala<br>260                         265                      270                      275 | 1351 |
| tct acc aat gga cag ctc tca gtc cac act ccc aaa agg gaa agt ttg<br>Ser Thr Asn Gly Gln Leu Ser Val His Thr Pro Lys Arg Glu Ser Leu<br>                    280                      285                      290 | 1399 |
| tcc cat gag gag cac ccc cat agc cat cct ctc tat gga cat ggt gta<br>Ser His Glu Glu His Pro His Ser His Pro Leu Tyr Gly His Gly Val<br>                295                      300                      305 | 1447 |
| tgc aag tgg cca ggc tgt gaa gca gtg tgc gaa gat ttc caa tca ttt<br>Cys Lys Trp Pro Gly Cys Glu Ala Val Cys Glu Asp Phe Gln Ser Phe<br>                310                      315                      320 | 1495 |
| cta aaa cat ctc aac agt gag cat gcg ctg gac gat aga agt aca gcc<br>Leu Lys His Leu Asn Ser Glu His Ala Leu Asp Asp Arg Ser Thr Ala<br>325                         330                      335 | 1543 |
| caa tgt aga gta caa atg cag gtt gta cag cag tta gag cta cag ctt<br>Gln Cys Arg Val Gln Met Gln Val Val Gln Gln Leu Glu Leu Gln Leu<br>340                         345                      350                      355 | 1591 |
| gca aaa gac aaa gaa cgc ctg caa gcc atg atg acc cac ctg cat gtg<br>Ala Lys Asp Lys Glu Arg Leu Gln Ala Met Met Thr His Leu His Val<br>                    360                      365                      370 | 1639 |
| aag tct aca gaa ccc aaa gcc gcc cct cag ccc ttg aat ctg gta tca<br>Lys Ser Thr Glu Pro Lys Ala Ala Pro Gln Pro Leu Asn Leu Val Ser<br>                375                      380                      385 | 1687 |
| agt gtc act ctc tcc aag tcc gca tcg gag gct tct cca cag agc tta<br>Ser Val Thr Leu Ser Lys Ser Ala Ser Glu Ala Ser Pro Gln Ser Leu<br>                    390                      395                      400 | 1735 |
| cct cat act cca acg acc cca acc gcc ccc ctg act ccc gtc acc caa<br>Pro His Thr Pro Thr Thr Pro Thr Ala Pro Leu Thr Pro Val Thr Gln<br>405                         410                      415 | 1783 |

```
ggc ccc tct gtc atc aca acc acc agc atg cac acg gtg gga ccc atc    1831
Gly Pro Ser Val Ile Thr Thr Thr Ser Met His Thr Val Gly Pro Ile
420                 425                 430                 435 cgc agg cgg tac tca gac aaa tac aac gtg ccc att tcg tca gca gat    1879
Arg Arg Arg Tyr Ser Asp Lys Tyr Asn Val Pro Ile Ser Ser Ala Asp
                    440                 445                 450 att gcg cag aac caa gaa ttt tat aag aac gca gaa gtt aga cca cca    1927
Ile Ala Gln Asn Gln Glu Phe Tyr Lys Asn Ala Glu Val Arg Pro Pro
            455                 460                 465 ttt aca tat gca tct tta att agg cag gcc att ctc gaa tct cca gaa    1975
Phe Thr Tyr Ala Ser Leu Ile Arg Gln Ala Ile Leu Glu Ser Pro Glu
        470                 475                 480 aag cag cta aca cta aat gag atc tat aac tgg ttc aca cga atg ttt    2023
Lys Gln Leu Thr Leu Asn Glu Ile Tyr Asn Trp Phe Thr Arg Met Phe
    485                 490                 495 gct tac ttc cga cgc aac gcg gcc acg tgg aag aat gca gtg cgt cat    2071
Ala Tyr Phe Arg Arg Asn Ala Ala Thr Trp Lys Asn Ala Val Arg His
500                 505                 510                 515 aat ctt agt ctt cac aag tgt ttt gtg cga gta gaa aac gtt aaa ggg    2119
Asn Leu Ser Leu His Lys Cys Phe Val Arg Val Glu Asn Val Lys Gly
                    520                 525                 530 gca gta tgg aca gtg gat gaa gta gaa ttc caa aaa cga agg cca caa    2167
Ala Val Trp Thr Val Asp Glu Val Glu Phe Gln Lys Arg Arg Pro Gln
            535                 540                 545 aag atc agt ggt aac cct tcc ctt att aaa aac atg cag agc agc cac    2215
Lys Ile Ser Gly Asn Pro Ser Leu Ile Lys Asn Met Gln Ser Ser His
        550                 555                 560 gcc tac tgc aca cct ctc aat gca gct tta cag gct tca atg gct gag    2263
Ala Tyr Cys Thr Pro Leu Asn Ala Ala Leu Gln Ala Ser Met Ala Glu
    565                 570                 575 aat agt ata cct cta tac act acc gct tcc atg gga aat ccc act ctg    2311
Asn Ser Ile Pro Leu Tyr Thr Thr Ala Ser Met Gly Asn Pro Thr Leu
580                 585                 590                 595 ggc aac tta gcc agc gca ata cgg gaa gag ctg aac ggg gca atg gag    2359
Gly Asn Leu Ala Ser Ala Ile Arg Glu Glu Leu Asn Gly Ala Met Glu
                    600                 605                 610 cat acc aac agc aac gag agt gac agc agt cca ggc aga tct cct atg    2407
His Thr Asn Ser Asn Glu Ser Asp Ser Ser Pro Gly Arg Ser Pro Met
            615                 620                 625 caa gcc gtg cat cct gta cac gtc aaa gaa gag ccc ctc gat cca gag    2455
Gln Ala Val His Pro Val His Val Lys Glu Glu Pro Leu Asp Pro Glu
        630                 635                 640 gaa gct gaa ggg ccc ctg tcc tta gtg aca aca gcc aac cac agt cca    2503
Glu Ala Glu Gly Pro Leu Ser Leu Val Thr Thr Ala Asn His Ser Pro
    645                 650                 655 gat ttt gac cat gac aga gat tac gaa gat gaa cca gta aac gag gac    2551
Asp Phe Asp His Asp Arg Asp Tyr Glu Asp Glu Pro Val Asn Glu Asp
660                 665                 670                 675 atg gag tga ctatcggggc gggccaaccc cgagaatgaa gattggaaaa            2600
Met Glu aggaaaaaaa aaaaaacacg tcaaaagtta gcagtgaaat tgttctccat tgttgtaca   2660 gtctggagga ttttcactac gttttgacaa ctctgaaatg tgttaactct tagtgccatc  2720
aagaacccca tttgggagta ttttgattt ttctactttt tgttgaaaaa aggaatttgt   2780
actctgtgca ttggatggac ttgtttggta cttgggattt tcctctctta accgtcaaca  2840
tcagtgttgt aaatttgcta aactgattca ctttttagcag cagactttga actgcagtcc 2900
tgccaacgtt ggacactgag gacgcccgac agagcttgtg cacctaagct gcagaccaag  2960
```

```
cctttgccca gaatttaagg attccaatgg acgacctatt tgcacagtac tgcatgttga    3020
ttatcactgc ctttactcct tttttttttt tttttttttt ttttttttg cttccagttg      3080 ggatggggaa ggcctttgtg tgtgtattgg ggggaggggt taaaaaataa ttatcccaaa    3140
ctttttaatg tattgctttt tttttttttt tttttccttc tactatacca ttttaagttc    3200
tgacctcagg cctccatttg ggccgatggc ctcttggagg cttaaagttt tctgtacctt    3260
gtgatgaatg ttaataggtg ttttttattat acaaagctga atgtcatttc tcgtttgtag   3320
ctttctgtca ctcattccat cttccttcag acatcaccac gtttctctaa agtcagaaaa   3380
cattccgttt tggtcttttt caaaaaggtc ccaaatgctg cactctacac atgaaggccc    3440
tctcacacag acgtgacgtc ctgccagaaa gagaatgaat gacagaaaaa aaaagagag     3500 acaaactcta ggaacaatgc cgattcattc cacgcagcag tattgggggt ggttcggggg   3560
aggggtgttt cggatttct tttttctttt tcttttcttt tttttttttt gcagcaacca    3620
ttaataaatg ccaccacatt ctaccagcac aaggaaacat aggcagcact gaaaaaaaaa   3680
aaaaagctca tattaattag actgacaata tggccttgga aggctctccc ttgtggaacc   3740
aagttgccat gggccttggg tgctctgcga taacgggtgt gggttggttt tgtttgcaaa   3800
atggccaaaa aaaaaaaccg gcttccccga gcagctgccc tgaaagtagg ggtggcggcg   3860
gcggcgctga gtttatacat tagttcagac ctacttggtg gcattaaact gtttgaatgc   3920
aaattcgatt tcagattgaa cttgttaagg gagttaacga gggctgagtt cagcaaatgc   3980
taaagtgtta atttcaaata tgcaaatttg gtactgcagt ttgttatgca atattatatc    4040
accaacccag tatcacaaaa actcatagaa gatatcatgt aggccctggg ctttgggggg   4100
gtcccaaaca tggtatgcag aaatgtgatg gttacaggtc agtacaacct cagtccttag    4160 aaccctcca cacttcagct ctgcacccac tttcctgtca tttatttata taggactgta    4220 gttttttta gttcgagagc ctttcgaagc ttaatttata ttctttcttt gtaccttttt     4280
tctaaaatta ccaaagatat tacacaaagg taaattatgt tctctgtttt atgctttatc    4340
tgatgaagcc aaatatcctc ttattgttga tcaaaggagg caaaagaatt tagaggcaaa    4400
tgacaagcga taggctattg caacctgaga aagagaactg ctccttcatc gtaaatttag    4460
aagaccaagt agataatgga accaaagttg ttactttttt ctagtagtta ttttttccttt   4520 ttctttttgt gtacctctac agagaccaaa actcattctc ttaaagagat tttatgggc    4580 tactgcagat aaaaatagga cacaatatta aaggagctac agaaggaagg gagtcccatc   4640
tcaaaaaaaa aatgaatgta tgccactgca attagagtat ccaataaagg agacagttta   4700
gagtcaggac agaaaagctt ccataattga actagattac ataatagtat ttctagaaaa   4760
agagatattt ttagattgta tgccactttt gtttaagaac tgtgctgtga tcactgtatt    4820
aattttggtt tatcttggca tatatccttc agtttgtttt tatttttaat ttttccttt    4880 tttccgatta ggctttggtc agcatttttc atttaaagaa aagtaacact cccatcccact   4940 cataagcttg gtacaaaaac ttctctggca gttactttg aagcttcact ctgctttctg    5000
tataaagggc agtctgtggt cacgcaagac tttaaaaaaa aaaaaaaaaa aaaaaaaaa    5060 aaaaaaaaaa aaaactttc caggcagctt catgatgtgc aggcagtagc cagacagggt    5120
catgggaagg gggccctgtg cttctaaact gagtggttgc tggttagttt ggtattcaaa   5180
agaggataaa aatctggtag attagttcat tctcagcatg tgtagctaga catgagtaaa   5240
gataacagca tgagaaactg ttagtacgca tacctcagtt caaaccttta gggaatgatt   5300
```

-continued

```
aaaatttaaa aaaaaaacat ttcactcagt tgcacttagt cgtatgtctt gcatgcttag    5360
tctaaagact gtagcaaaaa aaaaaaaaaa agaaaaatta gattttacat atctttgcag    5420
gtatcacagc cttgcagaag aaccaactga aaaaaaaatt ctcaggcttt acagcaagca    5480
aacttcacta tgattttttac aattctgatt ctgtatcccc tgggggttat cccagttgct    5540
tctttaggat ggggtttatt acgttgtaca tatatcccga tgtgtctgtg tgaatctttg    5600
tcttttttgg ggagggcag agggcggttc ttttttttaga tattgttcct aaaaaggaat    5660
aaatgcatac acctgtttgt caaaacacct ttgcttttttg tgcaactgct ttatattaac    5720
gatactaaaa aaaaatagct ttggaaaaaa aactactgta tgtaacggaa ttgcagaata    5780
tgctgcacat gtattttatt tagttatcct tgctttaaga atattggatg acatttcctg    5840
acatgtggga gggagaaact ccctaacttt ttttttctgc ttttaaactg taacatagtt    5900
gaagatttct ttttttctgtt ctcattgatt ggagcatttt gtacaggttt tgtgtgtgtg    5960
tgtgtgtgtg tgtgcgcgcg tgcgtgtgtg ttaatctgtt ttttgataca ttcctatccc    6020 ttgtgttttat cctaccactg ccttcctggc tatcttaaac aagttcatac atttgaaaag    6080 aaaaaaaaaat gttgtttaaa aaatgttttc tcctgctgca gtaaatattt tgcatgatga    6140
aattccaggg tcacactttt ccaagtttat cagtgaagta gtgattaaca atggggagtg    6200
tcaaaactat tgaacttttg tataaaaaaa aaaaaacttt acaaggtgcc aagatgtaaa    6260
gaaaatctgt tactttttttt ttctcaaaga aaagcataca ttagggaggt agtcccgtgt    6320
gtcagacaaa tgcactgtca ggaatgagga tccaacctac ctgtccctag agtccgtctt    6380
gtaagatgag ttaggctgcc ccttggacca gccacaaaat ggaatatcaa ggcttatgta    6440
catacgtgaa gagttaccac cagtcctgcc acctttggac agctctaaca ccatccccag    6500
catccagtca gacctagtaa agaaaacctt ggattcttaa cccaagatag gctgtaaatc    6560
actagctttt ttttcctcat gaaaaaaat agagttaaaa aatatttcct ctcttttcca    6620
tattccagct gaactccgtt tccaaaggca caaagaagag tgtgcttatt cagatttgat    6680
atctttttgg tacctttttgg ttaatgacat agcctcctga aattctggat gtcttcaaag    6740
tcagttttgc ttctttatcc tgaaaatcag atttacaatg ctgaaggcat ttcttgggcc    6800
cagtgtagct cacgcaatct ctgctaccca taagccttga tgaagatgat acagtccgga    6860
ctgtgagcat ggtgcttcat gtatatgtgc tgccagtaac aagaattttt ttgttttgtt    6920
ttgttttgtt ttgataaggc ataaagaaaa ctcattcctt gacatcaact gtaattccat    6980
cattccatgt ctgcggatac agacaataaa aaaatgttg tgtagtcagt actaattact    7040
gacattataa gcattctcaa atgcaataaa aatgctggtt gttcacgctg gtaaaaaaaa    7100
aa                                                                  7102
```

<210> SEQ ID NO 2
<211> LENGTH: 677
<212> TYPE: PRT
<213> ORGANISM: Homo sapiens

<400> SEQUENCE: 2

```
Met Met Gln Glu Ser Gly Thr Glu Thr Lys Ser Asn Gly Ser Ala Ile
1               5                   10                  15

Gln Asn Gly Ser Gly Gly Ser Asn His Leu Leu Glu Cys Gly Gly Leu
            20                  25                  30

Arg Glu Gly Arg Ser Asn Gly Glu Thr Pro Ala Val Asp Ile Gly Ala
        35                  40                  45
```

```
Ala Asp Leu Ala His Ala Gln Gln Gln Gln Gln Ala Leu Gln Val
 50                  55                  60

Ala Arg Gln Leu Leu Gln Gln Gln Gln Gln Gln Val Ser Gly
 65                  70                  75                  80

Leu Lys Ser Pro Lys Arg Asn Asp Lys Gln Pro Ala Leu Gln Val Pro
                 85                  90                  95

Val Ser Val Ala Met Met Thr Pro Gln Val Ile Thr Pro Gln Gln Met
            100                 105                 110

Gln Gln Ile Leu Gln Gln Gln Val Leu Ser Pro Gln Gln Leu Gln Val
            115                 120                 125

Leu Leu Gln Gln Gln Gln Ala Leu Met Leu Gln Gln Gln Gln Leu Gln
    130                 135                 140

Glu Phe Tyr Lys Lys Gln Gln Glu Gln Leu Gln Leu Gln Leu Leu Gln
145                 150                 155                 160

Gln Gln His Ala Gly Lys Gln Pro Lys Glu Gln Gln Val Ala Thr
            165                 170                 175

Gln Gln Leu Ala Phe Gln Gln Leu Leu Gln Met Gln Gln Leu Gln
            180                 185                 190

Gln Gln His Leu Leu Ser Leu Gln Arg Gln Gly Leu Leu Thr Ile Gln
            195                 200                 205

Pro Gly Gln Pro Ala Leu Pro Leu Gln Pro Leu Ala Gln Gly Met Ile
    210                 215                 220

Pro Thr Glu Leu Gln Gln Leu Trp Lys Glu Val Thr Ser Ala His Thr
225                 230                 235                 240

Ala Glu Glu Thr Thr Gly Asn Asn His Ser Ser Leu Asp Leu Thr Thr
                245                 250                 255

Thr Cys Val Ser Ser Ser Ala Pro Ser Lys Thr Ser Leu Ile Met Asn
            260                 265                 270

Pro His Ala Ser Thr Asn Gly Gln Leu Ser Val His Thr Pro Lys Arg
    275                 280                 285

Glu Ser Leu Ser His Glu Glu His Pro His Ser His Pro Leu Tyr Gly
    290                 295                 300

His Gly Val Cys Lys Trp Pro Gly Cys Glu Ala Val Cys Glu Asp Phe
305                 310                 315                 320

Gln Ser Phe Leu Lys His Leu Asn Ser Glu His Ala Leu Asp Asp Arg
            325                 330                 335

Ser Thr Ala Gln Cys Arg Val Gln Met Gln Val Val Gln Gln Leu Glu
            340                 345                 350

Leu Gln Leu Ala Lys Asp Lys Glu Arg Leu Gln Ala Met Met Thr His
    355                 360                 365

Leu His Val Lys Ser Thr Glu Pro Lys Ala Ala Pro Gln Pro Leu Asn
    370                 375                 380

Leu Val Ser Ser Val Thr Leu Ser Lys Ser Ala Ser Glu Ala Ser Pro
385                 390                 395                 400

Gln Ser Leu Pro His Thr Pro Thr Thr Pro Thr Ala Pro Leu Thr Pro
            405                 410                 415

Val Thr Gln Gly Pro Ser Val Ile Thr Thr Thr Ser Met His Thr Val
            420                 425                 430

Gly Pro Ile Arg Arg Arg Tyr Ser Asp Lys Tyr Asn Val Pro Ile Ser
            435                 440                 445

Ser Ala Asp Ile Ala Gln Asn Gln Glu Phe Tyr Lys Asn Ala Glu Val
    450                 455                 460

Arg Pro Pro Phe Thr Tyr Ala Ser Leu Ile Arg Gln Ala Ile Leu Glu
```

```
                465                 470                 475                 480
        Ser Pro Glu Lys Gln Leu Thr Leu Asn Glu Ile Tyr Asn Trp Phe Thr
                        485                 490                 495

Arg Met Phe Ala Tyr Phe Arg Arg Asn Ala Ala Thr Trp Lys Asn Ala
                        500                 505                 510

Val Arg His Asn Leu Ser Leu His Lys Cys Phe Val Arg Val Glu Asn
                        515                 520                 525

Val Lys Gly Ala Val Trp Thr Val Asp Glu Val Glu Phe Gln Lys Arg
                        530                 535                 540

Arg Pro Gln Lys Ile Ser Gly Asn Pro Ser Leu Ile Lys Asn Met Gln
        545                 550                 555                 560

Ser Ser His Ala Tyr Cys Thr Pro Leu Asn Ala Ala Leu Gln Ala Ser
                        565                 570                 575

Met Ala Glu Asn Ser Ile Pro Leu Tyr Thr Thr Ala Ser Met Gly Asn
                        580                 585                 590

Pro Thr Leu Gly Asn Leu Ala Ser Ala Ile Arg Glu Glu Leu Asn Gly
                        595                 600                 605

Ala Met Glu His Thr Asn Ser Asn Glu Ser Asp Ser Ser Pro Gly Arg
                        610                 615                 620

Ser Pro Met Gln Ala Val His Pro Val His Val Lys Glu Glu Pro Leu
        625                 630                 635                 640

Asp Pro Glu Glu Ala Glu Gly Pro Leu Ser Leu Val Thr Thr Ala Asn
                        645                 650                 655

His Ser Pro Asp Phe Asp His Asp Arg Asp Tyr Glu Asp Glu Pro Val
                        660                 665                 670

Asn Glu Asp Met Glu
                        675

<210> SEQ ID NO 3
<211> LENGTH: 19
<212> TYPE: RNA
<213> ORGANISM: Homo sapiens

<400> SEQUENCE: 3
aaucugggac ugagacaaa                                                     19

<210> SEQ ID NO 4
<211> LENGTH: 19
<212> TYPE: RNA
<213> ORGANISM: Homo sapiens

<400> SEQUENCE: 4
gaugcaagaa ucugggacu                                                     19

<210> SEQ ID NO 5
<211> LENGTH: 97
<212> TYPE: DNA
<213> ORGANISM: Homo sapiens

<400> SEQUENCE: 5
tgctgttgac agtgagcgcc ccaagaggaa tgacaaacaa tagtgaagcc acagatgtat        60
tgtttgtcat tcctcttggg atgcctactg cctcgga                                 97

<210> SEQ ID NO 6
<211> LENGTH: 19
<212> TYPE: DNA
<213> ORGANISM: Homo sapiens
```

```
<400> SEQUENCE: 6
ccaagaggaa tgacaaaca                                                 19

<210> SEQ ID NO 7
<211> LENGTH: 19
<212> TYPE: DNA
<213> ORGANISM: Homo sapiens

<400> SEQUENCE: 7
tgtttgtcat tcctcttgg                                                 19

<210> SEQ ID NO 8
<211> LENGTH: 97
<212> TYPE: DNA
<213> ORGANISM: Homo sapiens

<400> SEQUENCE: 8
tgctgttgac agtgagcgac agcaagttag tggattaaaa tagtgaagcc acagatgtat    60
tttaatccac taacttgctg ctgcctactg cctcgga                             97

<210> SEQ ID NO 9
<211> LENGTH: 19
<212> TYPE: DNA
<213> ORGANISM: Homo sapiens

<400> SEQUENCE: 9
agcaagttag tggattaaa                                                 19

<210> SEQ ID NO 10
<211> LENGTH: 19
<212> TYPE: DNA
<213> ORGANISM: Homo sapiens

<400> SEQUENCE: 10
tttaatccac taacttgct                                                 19

<210> SEQ ID NO 11
<211> LENGTH: 97
<212> TYPE: DNA
<213> ORGANISM: Homo sapiens

<400> SEQUENCE: 11
tgctgttgac agtgagcgac agcagcaagt tagtggatta tagtgaagcc acagatgtat    60
aatccactaa cttgctgctg ctgcctactg cctcgga                             97

<210> SEQ ID NO 12
<211> LENGTH: 19
<212> TYPE: DNA
<213> ORGANISM: Homo sapiens

<400> SEQUENCE: 12
agcagcaagt tagtggatt                                                 19

<210> SEQ ID NO 13
<211> LENGTH: 19
<212> TYPE: DNA
<213> ORGANISM: Homo sapiens

<400> SEQUENCE: 13
aatccactaa cttgctgct                                                 19
```

```
<210> SEQ ID NO 14
<211> LENGTH: 97
<212> TYPE: DNA
<213> ORGANISM: Homo sapiens

<400> SEQUENCE: 14
tgctgttgac agtgagcgac aggcggtact cagacaaata tagtgaagcc acagatgtat      60
atttgtctga gtaccgcctg ctgcctactg cctcgga                              97

<210> SEQ ID NO 15
<211> LENGTH: 19
<212> TYPE: DNA
<213> ORGANISM: Homo sapiens

<400> SEQUENCE: 15
aggcggtact cagacaaat                                                  19

<210> SEQ ID NO 16
<211> LENGTH: 19
<212> TYPE: DNA
<213> ORGANISM: Homo sapiens

<400> SEQUENCE: 16
atttgtctga gtaccgcct                                                  19

<210> SEQ ID NO 17
<211> LENGTH: 97
<212> TYPE: DNA
<213> ORGANISM: Homo sapiens

<400> SEQUENCE: 17
tgctgttgac agtgagcgac agcttcaact tttacaacaa tagtgaagcc acagatgtat      60
tgttgtaaaa gttgaagctg ctgcctactg cctcgga                              97

<210> SEQ ID NO 18
<211> LENGTH: 19
<212> TYPE: DNA
<213> ORGANISM: Homo sapiens

<400> SEQUENCE: 18
agcttcaact tttacaaca                                                  19

<210> SEQ ID NO 19
<211> LENGTH: 19
<212> TYPE: DNA
<213> ORGANISM: Homo sapiens

<400> SEQUENCE: 19
tgttgtaaaa gttgaagct                                                  19

<210> SEQ ID NO 20
<211> LENGTH: 97
<212> TYPE: DNA
<213> ORGANISM: Homo sapiens

<400> SEQUENCE: 20
tgctgttgac agtgagcgac agcttcaaga gtttttataaa tagtgaagcc acagatgtat     60
ttataaaact cttgaagctg ctgcctactg cctcgga                              97

<210> SEQ ID NO 21
<211> LENGTH: 19
<212> TYPE: DNA
```

<213> ORGANISM: Homo sapiens

<400> SEQUENCE: 21
agcttcaaga gttttataa                                              19

<210> SEQ ID NO 22
<211> LENGTH: 19
<212> TYPE: DNA
<213> ORGANISM: Homo sapiens

<400> SEQUENCE: 22
ttataaaact cttgaagct                                              19

<210> SEQ ID NO 23
<211> LENGTH: 97
<212> TYPE: DNA
<213> ORGANISM: Homo sapiens

<400> SEQUENCE: 23
tgctgttgac agtgagcgcg gacagtggat gaagtagaat tagtgaagcc acagatgtaa    60
ttctacttca tccactgtcc atgcctactg cctcgga                            97

<210> SEQ ID NO 24
<211> LENGTH: 19
<212> TYPE: DNA
<213> ORGANISM: Homo sapiens

<400> SEQUENCE: 24
gacagtggat gaagtagaa                                              19

<210> SEQ ID NO 25
<211> LENGTH: 19
<212> TYPE: DNA
<213> ORGANISM: Homo sapiens

<400> SEQUENCE: 25
ttctacttca tccactgtc                                              19

<210> SEQ ID NO 26
<211> LENGTH: 97
<212> TYPE: DNA
<213> ORGANISM: Homo sapiens

<400> SEQUENCE: 26
tgctgttgac agtgagcgcg gtaacccttc cctattaaa tagtgaagcc acagatgtat    60
ttaataaggg aagggttacc atgcctactg cctcgga                            97

<210> SEQ ID NO 27
<211> LENGTH: 19
<212> TYPE: DNA
<213> ORGANISM: Homo sapiens

<400> SEQUENCE: 27
gtaacccttc cctattaa                                               19

<210> SEQ ID NO 28
<211> LENGTH: 19
<212> TYPE: DNA
<213> ORGANISM: Homo sapiens

<400> SEQUENCE: 28
ttaataaggg aagggttac                                              19

```
<210> SEQ ID NO 29
<211> LENGTH: 97
<212> TYPE: DNA
<213> ORGANISM: Homo sapiens

<400> SEQUENCE: 29
tgctgttgac agtgagcgac aggcggtact cagacaaata tagtgaagcc acagatgtat     60
atttgtctga gtaccgcctg ctgcctactg cctcgga                              97

<210> SEQ ID NO 30
<211> LENGTH: 19
<212> TYPE: DNA
<213> ORGANISM: Homo sapiens

<400> SEQUENCE: 30
aggcggtact cagacaaat                                                  19

<210> SEQ ID NO 31
<211> LENGTH: 19
<212> TYPE: DNA
<213> ORGANISM: Homo sapiens

<400> SEQUENCE: 31
atttgtctga gtaccgcct                                                  19

<210> SEQ ID NO 32
<211> LENGTH: 97
<212> TYPE: DNA
<213> ORGANISM: Homo sapiens

<400> SEQUENCE: 32
tgctgttgac agtgagcgcc aggaacagtt gcagcttcaa tagtgaagcc acagatgtat     60
tgaagctgca actgttcctg ttgcctactg cctcgga                              97

<210> SEQ ID NO 33
<211> LENGTH: 19
<212> TYPE: DNA
<213> ORGANISM: Homo sapiens

<400> SEQUENCE: 33
aggaacagtt gcagcttca                                                  19

<210> SEQ ID NO 34
<211> LENGTH: 19
<212> TYPE: DNA
<213> ORGANISM: Homo sapiens

<400> SEQUENCE: 34
tgaagctgca actgttcct                                                  19

<210> SEQ ID NO 35
<211> LENGTH: 97
<212> TYPE: DNA
<213> ORGANISM: Homo sapiens

<400> SEQUENCE: 35
tgctgttgac agtgagcgcg ccaaatatcc tcttattgtt tagtgaagcc acagatgtaa     60
acaataagag atatttggc ttgcctactg cctcgga                               97

<210> SEQ ID NO 36
```

```
<211> LENGTH: 19
<212> TYPE: DNA
<213> ORGANISM: Homo sapiens

<400> SEQUENCE: 36
ccaaatatcc tcttattgt                                                  19

<210> SEQ ID NO 37
<211> LENGTH: 19
<212> TYPE: DNA
<213> ORGANISM: Homo sapiens

<400> SEQUENCE: 37
acaataagag gatatttgg                                                  19

<210> SEQ ID NO 38
<211> LENGTH: 97
<212> TYPE: DNA
<213> ORGANISM: Homo sapiens

<400> SEQUENCE: 38
tgctgttgac agtgagcgcg gtaacccttc ccttattaaa tagtgaagcc acagatgtat     60
ttaataaggg aagggttacc atgcctactg cctcgga                              97

<210> SEQ ID NO 39
<211> LENGTH: 19
<212> TYPE: DNA
<213> ORGANISM: Homo sapiens

<400> SEQUENCE: 39
gtaacccttc ccttattaa                                                  19

<210> SEQ ID NO 40
<211> LENGTH: 19
<212> TYPE: DNA
<213> ORGANISM: Homo sapiens

<400> SEQUENCE: 40
ttaataaggg aagggttac                                                  19

<210> SEQ ID NO 41
<211> LENGTH: 57
<212> TYPE: DNA
<213> ORGANISM: Homo sapiens

<400> SEQUENCE: 41
ccggcgcaga agttagacca ccattctcga gaatggtggt ctaacttctg cgttttt        57

<210> SEQ ID NO 42
<211> LENGTH: 21
<212> TYPE: DNA
<213> ORGANISM: Homo sapiens

<400> SEQUENCE: 42
cgcagaagtt agaccaccat t                                               21

<210> SEQ ID NO 43
<211> LENGTH: 21
<212> TYPE: DNA
<213> ORGANISM: Homo sapiens

<400> SEQUENCE: 43
aatggtggtc taacttctgc g                                               21
```

<210> SEQ ID NO 44
<211> LENGTH: 57
<212> TYPE: DNA
<213> ORGANISM: Homo sapiens

<400> SEQUENCE: 44
ccgggcagca agttagtgga ttaaactcga gtttaatcca ctaacttgct gcttttt          57

<210> SEQ ID NO 45
<211> LENGTH: 21
<212> TYPE: DNA
<213> ORGANISM: Homo sapiens

<400> SEQUENCE: 45
gcagcaagtt agtggattaa a                                                 21

<210> SEQ ID NO 46
<211> LENGTH: 21
<212> TYPE: DNA
<213> ORGANISM: Homo sapiens

<400> SEQUENCE: 46
tttaatccac taacttgctg c                                                 21

<210> SEQ ID NO 47
<211> LENGTH: 57
<212> TYPE: DNA
<213> ORGANISM: Homo sapiens

<400> SEQUENCE: 47
ccgggcccat tcgtcagca gatatctcga gatatctgct gacgaaatgg gctttt            57

<210> SEQ ID NO 48
<211> LENGTH: 21
<212> TYPE: DNA
<213> ORGANISM: Homo sapiens

<400> SEQUENCE: 48
gcccatttcg tcagcagata t                                                 21

<210> SEQ ID NO 49
<211> LENGTH: 21
<212> TYPE: DNA
<213> ORGANISM: Homo sapiens

<400> SEQUENCE: 49
atatctgctg acgaaatggg c                                                 21

<210> SEQ ID NO 50
<211> LENGTH: 57
<212> TYPE: DNA
<213> ORGANISM: Homo sapiens

<400> SEQUENCE: 50
ccgggtgcga agatttccaa tcattctcga gaatgattgg aaatcttcgc acttttt          57

<210> SEQ ID NO 51
<211> LENGTH: 21
<212> TYPE: DNA
<213> ORGANISM: Homo sapiens

<400> SEQUENCE: 51

-continued

```
gtgcgaagat ttccaatcat t                                              21

<210> SEQ ID NO 52
<211> LENGTH: 21
<212> TYPE: DNA
<213> ORGANISM: Homo sapiens

<400> SEQUENCE: 52
aatgattgga aatcttcgca c                                              21

<210> SEQ ID NO 53
<211> LENGTH: 57
<212> TYPE: DNA
<213> ORGANISM: Homo sapiens

<400> SEQUENCE: 53
ccggcaggct tcaatggctg agaatctcga gattctcagc cattgaagcc tgttttt       57

<210> SEQ ID NO 54
<211> LENGTH: 21
<212> TYPE: DNA
<213> ORGANISM: Homo sapiens

<400> SEQUENCE: 54
caggcttcaa tggctgagaa t                                              21

<210> SEQ ID NO 55
<211> LENGTH: 21
<212> TYPE: DNA
<213> ORGANISM: Homo sapiens

<400> SEQUENCE: 55
attctcagcc attgaagcct g                                              21
```